United States Patent
Hu

(10) Patent No.: US 11,202,773 B2
(45) Date of Patent: Dec. 21, 2021

(54) LOCALLY BIOAVAILABLE DRUGS

(71) Applicant: UNIVERSITY OF HOUSTON SYSTEM, Houston, TX (US)

(72) Inventor: Ming Hu, Bellaire, TX (US)

(73) Assignee: University of Houston System, Houston, TX (US)

( * ) Notice: Subject to any disclaimer, the term of this patent is extended or adjusted under 35 U.S.C. 154(b) by 8 days.

(21) Appl. No.: 15/568,195

(22) PCT Filed: Apr. 20, 2016

(86) PCT No.: PCT/US2016/028371
§ 371 (c)(1),
(2) Date: Oct. 20, 2017

(87) PCT Pub. No.: WO2016/172159
PCT Pub. Date: Oct. 27, 2016

(65) Prior Publication Data
US 2018/0098965 A1    Apr. 12, 2018

Related U.S. Application Data

(60) Provisional application No. 62/149,931, filed on Apr. 20, 2015.

(51) Int. Cl.
*A61K 31/4155*    (2006.01)
*A61K 31/415*    (2006.01)

(52) U.S. Cl.
CPC ........ *A61K 31/4155* (2013.01); *A61K 31/415* (2013.01)

(58) Field of Classification Search
CPC .......................... A61K 31/4155; A61K 31/414
See application file for complete search history.

(56) References Cited

PUBLICATIONS

Ruiz et al. (Bioorganic and Medicinal Chemistry Letters (2011) 21:6636-6640, (Year: 2011).*
Pommery et al. (J. Med. Chem. (2004) 47: 6195-6206). (Year: 2004).*
Desai et al. (International Journal of Cancer (2010) 127:230-238). (Year: 2010).*
Desai et. al. (Chemico-Biological Interactions (2010) 446-456). (Year: 2010).*
Pommery et al. (J. Med. Chern. (2004) 47:6195-6206). (Year: 2004).*
Smith et al. (March's Advanced Organic Chemistry, fifth edition, Jon Wiley (2001), pp. 390-391, 445 and 449). (Year: 2001).*
International Preliminary Report on Patentability dated Nov. 2, 2017, in international Application No. PCT/US16/28371.
Beswick, Paul J., et al.; Identification and optimisation of a novel series of pyrimidine based cyclooxygenase-2 (COX-2) inhibitors. Utilisation of a biotransformation approach; Bioorganic; 2009; pp. 4509-4514: vol. 19; Elsevier Ltd.
Bashir, Rafia, et al.; Synthesis of some new 1,3,5-trisubstituted pyrazolines bearing benzene sulfonamide as anticancer and anti-inflammatory agents; Bioorganic; 2011; pp. 4301-4305; vol. 21; Elsevier Ltd.
Ruiz, Juan F. Marquez, et al.; A double prodrug system for colon targeting of benzenesulfonamide COX-2 inhibitors Bioorganic; 2011; pp. 6636-6640; vol. 21; Elsevier Ltd.
Bano, Sameena, et al.; Synthesis and biological evaluation of some new 2-pyrazolines bearing benzene sulfonamide moiety as potential anti-inflammatory and anti-cancer agents; European Journal of Medicinal Chemistry; 2011; pp. 5763-5768; vol. 46; Elsevier Ltd.
Procopiou, Panayiotis A., et al.; Synthesis and Structure—Activity Relationships of Long-Acting B2 Adrenergic Receptor Agonists Incorporating Metabolic Inactivation: An Antedrug Approach; Journal of Medicinal Chemistry; 2010 pp. 4522-4530; vol. 53; American Chemical Society.
Bertagnolli, Monica M.; Chemoprevention of colorectal cancer with cyclooxygenase-2 inhibitors: two steps forward, one step back; Lancet Oncology; May 2007; pp. 439-443; vol. 8; Brigham and Women's Hospital; Boston, MA.
Bodor, Nicholas, et al.; Soft Drug Design: General Principles and Recent Applications; 2000; pp. 58-101; Center for Drug Discovery, University of Florida, Health Science Center, Gainesville, Florida; John Wiley & Sons, Inc.

* cited by examiner

*Primary Examiner* — Marcos L Sznaidman
(74) *Attorney, Agent, or Firm* — Jackson Walker LLP

(57) ABSTRACT

Drugs have been designed and developed with a structural motif allowing local bioavailability in the target organ but that are not broadly distributed at a concentration sufficient to illicit toxic side effects in non-targeted organs. The structural motif subjects the compound to be rapidly metabolized by metabolic enzymes before reaching the non-targeted organs.

1 Claim, 30 Drawing Sheets

| Compound | R₁ | R₂ | Compound | R₁ | R₂ |
|---|---|---|---|---|---|
| 6a1 | CH₃ | 2'-OH | 6c1 | OCH₃ | 2'-OH |
| 6a2 | CH₃ | 3'-OH | 6c2 | OCH₃ | 3'-OH |
| 6a3 | CH₃ | 4'-OH | 6c3 | OCH₃ | 4'-OH |
| 6b1 | H | 2'-OH | | | |
| 6b2 | H | 3'-OH | 7a1 | CH₃ | 2'-OH |
| 6b3 | H | 4'-OH | 7a'3 | CH₃ | 2'-OCH₃ |

# LOCALLY BIOAVAILABLE DRUGS

CROSS-REFERENCE TO RELATED APPLICATIONS

This application is the National Stage of International Application No. PCT/US2016/028371, filed Apr. 20, 2016; which claims the benefit of U.S. Provisional Application No. 62/149,931, filed Apr. 20, 2015; both of which are incorporated by reference in their entirety herein.

GOVERNMENT LICENSE RIGHTS

This invention was made with government support under GM070737 awarded by National Institutes of Health. The government has certain rights in the invention.

FIELD

The present disclosure relates to compositions and methods to target certain organs for therapeutic treatment. More specifically, the present disclosure pertains to targeting certain organs for therapeutic treatment with high concentrations of therapeutic drugs while avoiding the targeting of the same or similar therapeutic drugs in organs that may be harmed or not in need of treatment by therapeutic drugs.

BACKGROUND

Most drugs, especially those of the orally administered drugs, are systemically bioavailable, and as such have broad distribution throughout the body. This is often necessary since site of drug administration is different from site of action, and broad distribution allows drugs to gain access to distant target sites. Because of this need to gain broad distribution, medicinal chemists are often rewarded to make drugs that are highly bioavailable systemically so the drugs may be used to treat multiple diseases in different organs.

To make the drugs broadly bioavailable, medicinal chemists often design their orally administered drugs to avoid first-pass metabolism. Separately, medicinal chemists also avoid including structures that will make drugs susceptible to rapid phase II drug metabolism or enterohepatic recycling, both of which will limit their systemic distribution. Avoidance of first-pass metabolism and enterohepatic recycling is rather challenging since both are normal physiological processes. Therefore, making small molecular drugs bioavailable is often a major milestone during the development of a drug.

The need to make drugs highly bioavailable systemically creates a toxicity problem for many drugs. Both "on-target" and "off target" toxicities may occur, which could limit a drug's potential market or lead to its withdrawal from the market. It is quite common that a drug's therapeutic targets and toxicity targets reside in different organs. However, because most of these drugs are highly bioavailable systemically, they are often present at the same or even higher concentrations in the organs that are adversely affected by the toxicities than those organs that are targets for the therapeutic effects.

Orally bioavailable COX-2 inhibitors are a subclass of nonsteroidal anti-inflammatory drugs (NSAIDs) that selectively block the COX-2 enzyme and not the COX-1 enzyme. Blocking the COX-2 enzyme impedes the production of proinflammatory prostaglandins which is often the cause of the pain and swelling. Proinflammatory prostaglandins are also signal molecules that promote tumor growth and cancer development. Because the COX-2 inhibitors selectively block the COX-2 enzyme and not the COX-1 enzyme, these drugs are uniquely different from traditional NSAIDs, which usually block both COX-1 and COX-2 enzymes and can cause major gastrointestinal bleeding in certain patients. Therefore, COX-2 inhibitors initially enjoyed tremendous commercial success with sales in the billions of dollars.

Unfortunately, it was found that these COX-2 inhibitors have serious side effects that can lead to higher incidence of death due to cardiac toxicity. One of such COX-2 inhibitors Vioxx was withdrawn from the market because of this risk, and it is likely to cost more than $4.85 billion in litigation costs for the company Merck [8]. Because of this huge liability, several COX-2 inhibitors were voluntarily withdrawn from the market and many more were not further developed [9]. A recent patent search found that many of the patents on COX-2 inhibitors were abandoned by their owners prior to their expiration dates. No new COX-2 inhibitors are currently on the development pipeline.

Even though clinical application of COX-2 inhibitors is severely limited by their reported cardiac toxicity risks, the only COX-2 inhibitor on the US market celecoxib ("Celebrex") still had annual sales exceeding 2 billion dollars in 2014, the last year with full patent protection. Hence, COX-2 inhibitors represent an important class of drugs that can meet the needs of certain patients. Importantly, the regular NSAIDs are still among the top 5 most popular drugs used by humans.

Millions of patients each year are prevented from receiving the benefit from using COX-2 inhibitors because of reported cardiac toxicities. In addition, tens of thousands of patients suffering from pain will ingest higher than the recommended doses of acetaminophen, leading to hundreds of deaths per year in United Stated alone, according to the Poison Control Centers [10]. Hence, there is a medical need to design additional COX-2 inhibitors that do not have cardiac toxicity but are effective at their target organs.

Previously, in large trials using Celebrex and Vioxx, it was shown that both drugs were highly effective in preventing the reoccurrence of sporadic adenomas, a precancerous lesion highly indicative of future colon cancer development. Celebrex was also approved for treating familial adenomatous polyposis (FAP), a genetic disorder that will lead to colon cancer and early death if not treated. However, FAP indication was withdrawn and colon cancer chemoprevention was not approved because of the previously described cardiac toxicity.

Cardiac toxicity of current COX-2 inhibitors is related to its broad distribution. Celecoxib has displayed a plasma concentration of 5 µM in humans, at least 5000 times higher than its $IC_{50}$ values against COX-2 enzyme [6, 7]. As a consequence, celecoxib or other NSAIDs cannot be used in colon cancer chemoprevention or in the management of chronic pain (i.e., they cannot be used for long periods of time) for the vast majority of the patients. Therefore, the need to design COX-2 inhibitors with local bioavailability in colon but no systemic bioavailability is apparent.

Towards fulfilling this need, building a drug such as a locally bioavailable COX-2 inhibitor with a structural motif that will subject the compound to rapid first-pass metabolism before reaching the systemic circulation will limit its exposure to non-therapeutically targeted organs affected by toxicity. Such a drug tailored to have bioavailability only in a specific organ will be of great benefit in the alleviation of pain in the colon and using such drugs as chemotherapeutic and/or chemopreventive agents in certain targeted organs (e.g., colon).

SUMMARY

An embodiment of the disclosure is a composition comprising a therapeutic compound designed with a designated structural motif; wherein the designated structural motif allows therapeutic effects at the targeted organ; wherein the designated structural motif causes increased metabolism of the therapeutic compound; and wherein the toxic effects of the therapeutic compound are decreased or virtually eliminated outside of the target organ. In an embodiment, the therapeutic compound is a COX-2 inhibitor. In an embodiment, the therapeutic compound is selected from the group consisting of a glucose transporter (SGLT2) inhibitors, Niemann-Pick C1-like 1 protein inhibitors, TNFα inhibitors, FXR agonists, anti-inflammatory cytokines, and steroidal anti-inflammatory drugs. In an embodiment, the structural motif is a phenolic, an amine, an aliphatic alcohol, a carboxylic acid, or a sulfhydryl. In an embodiment, the target organ is intestine. In an embodiment, the toxic effects affect a patient's heart. In an embodiment, the therapeutic compound is selected from the group consisting of 6a1, 6c1, and 7a1 (FIG. 1). In an embodiment, the therapeutic compound is metabolized by an enzyme selected from the group consisting of UDP-glucuronosyltransferases (UGTs), sulfotransferases (SULTs), esterases, glutathione transferases (GT), cytochrome P450 enzymes, and hydrolases. In an embodiment, at least one of the therapeutic compounds and metabolites of the therapeutic compounds are substrates of hepatic uptake transporters selected from the group consisting of organic anion transporting polypeptides (OATPs), organic anion transporters (OATs), and other uptake transporters capable of the same function. In an embodiment, at least one of the therapeutic compounds and metabolites of the therapeutic compounds are substrates of hepatic efflux transporters selected from the group consisting of multidrug-resistance related protein 2 (MRP2), breast cancer resistance protein (BCRP), bile salt efflux protein (BSEP), and other efflux transporter capable of the same function.

An embodiment of the disclosure is a method of drug design comprising modifying a therapeutic compound with a structural motif; and increasing metabolism of the therapeutic compound; wherein the concentration outside of the therapeutic target organ is decreased in comparison to the therapeutic compound without the added structural motif. In an embodiment, the therapeutic compound is a COX-2 inhibitor. In an embodiment, the therapeutic compound is selected from the group consisting of a glucose transporter (SGLT2) inhibitors, Niemann-Pick C 1-like 1 protein inhibitors, TNFα inhibitors, FXR agonists, anti-inflammatory cytokines, and steroidal anti-inflammatory drugs. In an embodiment, the structural motif is a phenolic, an amine, an aliphatic alcohol, a carboxylic acid, or a sulfhydryl. In an embodiment, the target organ is intestine. In an embodiment, toxic effects of the therapeutic compound are decreased outside of a target organ. In an embodiment, the therapeutic compound is selected from the group consisting of 6a1, 6c1, and 7a1 (FIG. 1). In an embodiment, the therapeutic compound is metabolized by an enzyme selected from the group consisting of UDP-glucuronosyltransferases (UGTs), sulfotransferases (SULTs) esterases, glutathione transferases (GT), cytochrome P450 enzymes, and hydrolases. In an embodiment, at least one of the therapeutic compounds and metabolites of the therapeutic compounds are substrates of hepatic uptake transporters selected from the group consisting of organic anion transporting polypeptides (OATPs), organic anion transporters (OATs), and other uptake transporters capable of the same function. In an embodiment, at least one of the therapeutic compounds and metabolites of the therapeutic compounds are substrates of hepatic efflux transporters selected from the group consisting of multidrug-resistance related protein 2 (MRP2), breast cancer resistance protein (BCRP), bile salt efflux protein (BSEP), and other efflux transporter capable of the same function.

Other objects, features, and advantages of the present disclosure will become apparent from the following detailed description. It should be understood, however, that the detailed description and the specific examples, while indicating embodiments of the disclosure, are given by way of illustration only, since various changes and modifications within the spirit and scope of the disclosure will become apparent to those skilled in the art from this detailed description.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which:

FIG. 10A illustrates UPLC-UV analysis of the bile samples collected from rats before (upper, Blank Bile) and during (middle, 6a1 glucuronide in bile) the perfusion of β-CD-formulated 70 µM 6a1 in HBSS. The large peak eluted between 2.8 and 2.9 minutes was identified as the glucuronide of 6a1, because it was shown to be converted to 6a1 by β-glucuronidase (lower, 6a1 in bile).

FIG. 10B illustrates the amounts of 6a1 absorbed in colon and excreted as glucuronide in bile each hour during the perfusion period.

FIG. 11A shows the blood concentrations of celecoxib at different time points when the rat colon was perfused with different concentrations of celecoxib.

FIG. 11B shows blood concentrations of 6a1 at different time points when the rat colon was perfused with 10 µM 6a1 in HBSS or β-CD-formulated 70 µM 6a1 in HBSS. The contents of the phase II metabolites of 6a1 were below quantitation limit and therefore negligible in all the blood samples.

DETAILED DESCRIPTION

Figure 1:
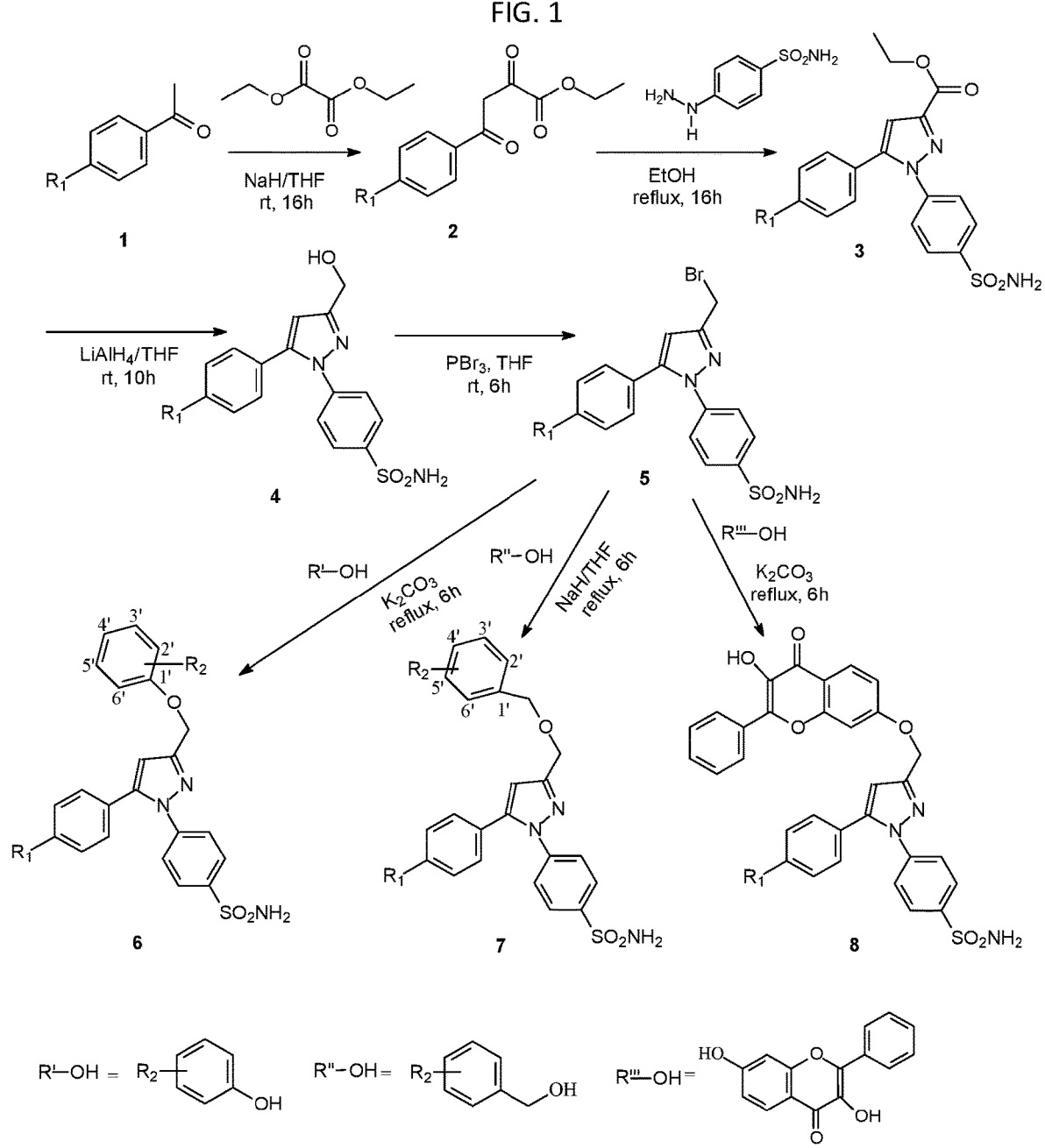
FIG. 1 is an illustration of the chemical structures of the locally bioavailable COX-2 inhibitors and a representative synthesis scheme. The locally bioavailable COX-2 inhibitors were prepared by several steps with the agents and conditions indicated in this scheme. All the compounds were purified by silica gel chromatography, probed using LC-MS/MS, and certified (or verified) with nuclear magnetic resonance (NMR).

The particulars shown herein are by way of example and for purposes of illustrative discussion of the certain embodiments of the present disclosure only and are presented in the cause of providing what is believed to be the most useful and readily understood description of the principles and conceptual aspects of various embodiments of the disclosure. In this regard, no attempt is made to show structural details of the disclosure in greater detail than is necessary for the fundamental understanding of the disclosure, the description should be taken with the drawings making apparent to those skilled in the art how the several forms of the disclosure can be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3rd Edition.

As used herein, the term "mammal" is known in the art, and exemplary mammals include humans, primates, bovines, porcines, ovines, equines, caprines, canines, felines, and rodents (e.g., mice and rats).

As used herein, the term "patient," means and refers to either a human or non-human mammal.

The "Central Theme" is to develop methods, approaches, and evaluation systems to develop drugs with narrow distribution and high local bioavailability by harnessing the power of the body's own physiological processes. Each of these processes may include at least enzymes, transporters, and biological rhythm that humans already possess. The key is to design drug molecules that can take advantage of these physiological processes for the development of safe and effective drugs.

In an embodiment, this "Central Theme" is demonstrated by locally bioavailable cyclooxygenase-2 (COX-2) inhibitors for treating colonic diseases that are mediated by COX-2. This "Central Theme" can be used to design other classes of drugs to treat colonic diseases using methods, approaches and evaluation systems described here. The "Central Theme" can also be used to design drugs to treat other diseases of the gastrointestinal tract.

Many drugs' therapeutic targets and toxicity targets are in different organs. However, most of these drugs are systemically bioavailable, and as such have broad distribution throughout the body, i.e., they are often present at the same or even higher concentrations at the organs responsible for the toxicity than that for the therapeutic effects. Disclosed herein are the design and development of drugs that have local bioavailability in the target organ but are not broadly distributed at high-enough concentration to illicit toxic side effects in non-targeted organs. The approach used is to build in a structural motif that subjects the compound to be rapidly metabolized by phase I or phase II enzymes presented in humans before reaching the non-targeted organs responsible for toxicity. Locally bioavailable COX-2 inhibitors for colonic diseases disclosed in detail here demonstrate the principle by using a class of phase II enzymes called UGTs. The power of first-pass metabolism and enterohepatic recycling, two normal physiological processes, can be harnessed to achieve these goals.

A series of locally bioavailable COX-2 inhibitors for colonic diseases were purposefully designed and obtained to be locally active but lack the systemic bioavailability. Such an approach would decrease or eliminate the cardiovascular toxicity associated with current systemically available COX-2 inhibitors. COX-2 inhibitors have been shown repeatedly in animal and human studies to be active against colorectal cancer (CRC) [1-3], and precancerous lesions in colon (e.g., familial adenomatous polyposis or FAP).

Disclosed herein are locally active COX-2 inhibitors that are not systemically bioavailable, and therefore will not cause cardiovascular toxicity, and methods of preparation of the locally active COX-2 inhibitors. Locally bioavailable COX-2 inhibitors can be used for colon cancer prevention, precancerous lesions, and intestinal inflammation-related diseases-. This concept can be applied to additional therapeutic classes whose therapeutic target is in the intestinal lumen but whose toxic side effect targets are not. In various embodiments, the drug can be glucose transporter (SGLT2) inhibitors that treat diabetes, for cholesterol absorption (Niemann-Pick C1-like 1, NPC1L1 protein) inhibitors that treat hyperlipidemia, and for steroidal anti-inflammatory drugs that treat colonic diseases.

Systemically available COX-2 inhibitors are toxic to the cardiovascular system [4, 5]. Building certain structural motifs into COX-2 inhibitors makes them excellent substrates for hepatic UDP-glucuronosyltransferases (UGTs) and sulfotransferases (SULTs). These structural motifs will make the compounds unavailable to the systemic circulation, thereby eliminating any toxicity associated with the systemic exposure (such as cardiovascular toxicities). Disclosed herein are lead compounds with the above stated structural motifs.

The present disclosure relates to building structural motifs into drugs to create new therapeutic compounds that will be rapidly metabolized before reaching the non-targeted organs responsible for toxicity. In various embodiments, other structural motifs that can be used to modify the therapeutic compounds that include but are not limited to phenolic rings, aromatic alcohols, flavonoids, coumarins, stilbenoids, ligands, amino acids, choline and so on. In certain embodiments, the target organs can include but are not limited to the stomach, small intestine, colon, liver, and joints.

In certain embodiments of the disclosure, structural motifs are incorporated into therapeutic drugs to make the now new compound a substrate for hepatic UDP-glucuronosyltransferases (UGTs) and sulfotransferases (SULTs). In various embodiments, incorporating structural motifs into a therapeutic drug can make the new compound a substrate for other mammalian, and more specifically, human enzymes including but not limited to catechol-O-methyl transferase (COMT), glutathione S-transferases (GSTs), N-acetyltransferases, bile acid-CoA:amino acid N-acyltransferase, choline acetyltransferase (ChAT), glycine-N-acyltransferase (GLYAT), aspartate aminotransferase (AST), alanine aminotransferase (ALT), phenylalanine hydroxylase, cerebrosidase, β-hexosaminidase A, α-iduronidase, and iduronate sulfatase, cytochrome P-450 enzymes (CYPs), esterases, and other hydrolases.

In certain further embodiments, the introduced structural motifs result in the compounds being generally unavailable to systemic circulation. In such embodiments, the unavailability eliminates or reduces toxicities associated with systemic exposure. In various embodiments, the toxicities reduced include but are not limited to cardiovascular toxicity, neurotoxicity, hepatotoxicity, immunotoxicity, nephrotoxicity, pulmonary toxicity, ototoxicity, ocular toxicity, muscle toxicity, skin toxicity, skeletal toxicity, hematotoxicity, splenic toxicity, pancreatic toxicity, reproductive toxicity, endocrine toxicity, and fetal toxicity.

In an embodiment, delivery routes that can be utilized include but are not limited to enteral (or oral), parenteral, sublingual, respiratory, ophthalmic, otologic, nasal, urogenital, dermal, and injection (including but not limited to intradermal, subcutaneous, transdermal, intramuscular, intracavernous, intravitreal, intra-articular, trans scleral, intracerebral, intrthecal, epidural, intravenous, intracardiac, intramuscular, interosseous, and intraperitoneal).

The first class of compounds useful in treating cyclooxygenase-2 mediated diseases is defined by Formula I.

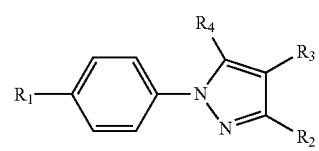

(1)

wherein $R_1$ is selected from sulfamyl, substituted sulfamyl, halo, alkyl, alkoxy, hydroxyl, and haloalkyl.
wherein R2 is selected from hydrido, halo, haloalkyl, cyano, nitro, formyl, carboxyl, alkoxycarbonyl, carboxyalkyl, alkoxycarbonylalkyl, amidino, cyanoamidino, arnido, alkoxy, amidoalkyl, N-monoalkylamido, N-monoarylamido, N,N-dialkyla-mido, N-alkyl-N-arylamido, alkylcarbonyl, alkylcarbo-nylalkyl, hydroxyalkyl, alkylthio, alkylsulfinyl, alkyl-sulfonyl, N-alkylsulfamyl, N-arylsulfamyl, arylsulfonyl, N,N-dialkylsulfamyl, N-alkyl-N-arylsulfamyl, and heterocyclic when $R_3$ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

wherein $R_3$ is selected from hydrido, halo, haloalkyl, cyano, nitro, formyl, carboxyl, alkoxycarbonyl, carboxyalkyl, alkoxycarbonylalkyl, amidino, cyanoamidino, arnido, alkoxy, amidoalkyl, N-monoalkylamido, N-monoarylarnido, N,N-dialkyla-mido, N-alkyl-N-arylarnido, alkylcarbonyl, alkylcarbo-nylalkyl, hydroxyalkyl, alkylthio, alkylsulfinyl, alkyl-sulfonyl, N-alkylsulfamyl, N-arylsulfamyl, arylsulfonyl, N,N-dialkylsulfamyl, N-alkyl-N-arylsulfamyl, heterocyclic, heterocycloalkyl, and aralkyl when $R_2$ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

wherein $R_4$ is selected from aryl, cycloalkyl, cycloalkenyl and heterocyclic; wherein $R_4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy hydroxyalkyl haloalkoxy, sulfamyl, N-alkylsulfamyl, amino, methylthio, N-alkylarnino, N,N-dialkylamino, heterocyclic, nitro and acylarnino;

Or wherein $R_3$ and $R_4$ together form nosulfonyl]phenyl)-5-phenylpyrazole-3-carboxylic acid has been prepared from the above described 4-[3-methyl-5-65 phenyl-1H-pyrazol-1-yl]benzenesulfonamide compound

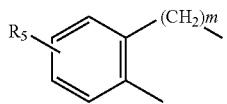

wherein $R_5$ is one or more radicals selected from halo, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylarnido, haloalkyl, hydrido, hydroxyl, alkoxy, hydroxyalkyl, haloalkoxy, sulfamyl, N-alkylsulfamyl, amino, alkylamino, heterocyclic, nitro and acylarnino; provided $R_2$ and $R_3$ are not identical radicals selected from hydrido, carboxyl and ethoxycarbonyl; further provided that $R_2$ cannot be carboxyl when $R_3$ is hydrido and when $R_4$ is phenyl; and further provided that $R_4$ is sulfamyl or N-alkylsulfamyl when $R_1$ is halo; or a pharmaceutically-acceptable salt thereof when $R_2$ or $R_3$ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

The phrase "further provided", as used in the above description, is intended to mean that the denoted proviso is not to be considered conjunctive with any of the other provisos.

A preferred class of compounds consists of those compounds of Formula 1 wherein R1 is sulfamyl or substituted sulfamyl, wherein R2 is selected from phenyl with one or more hydroxyl, alkylphenyl with one or more hydroxyl, wherein R3 is from hydrido, halo, wherein R4 is selected from aryl with substitute of methyl, methoxyl, halo, hydrido, or methylthio and pharmaceutically acceptable salts thereof.

Example structures are listed below.

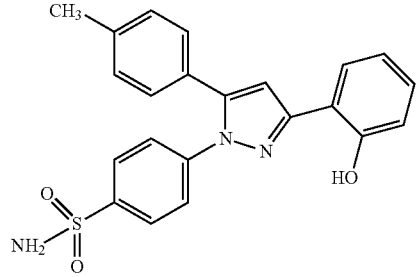

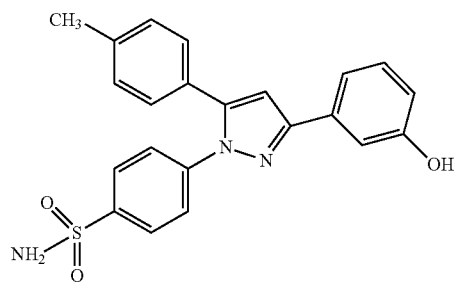

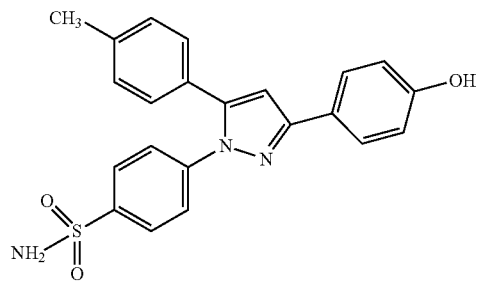

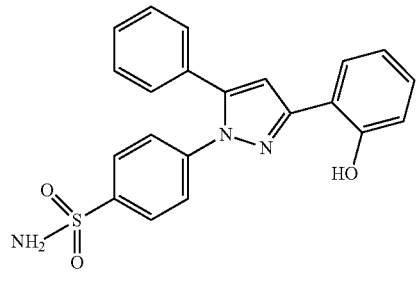

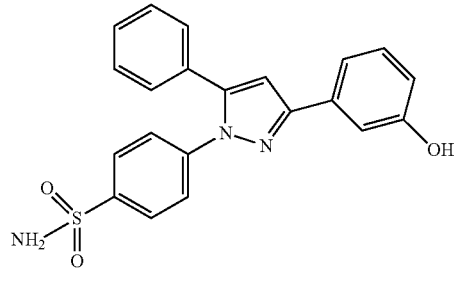

-continued
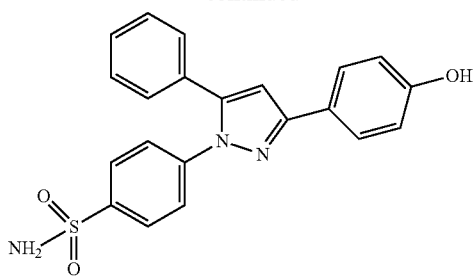
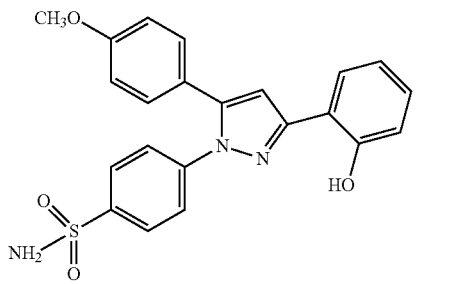
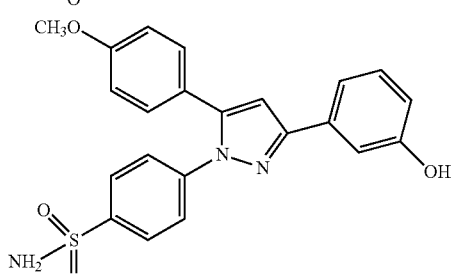
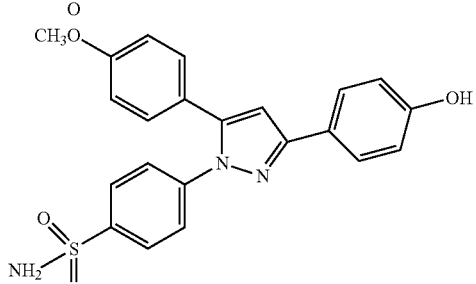
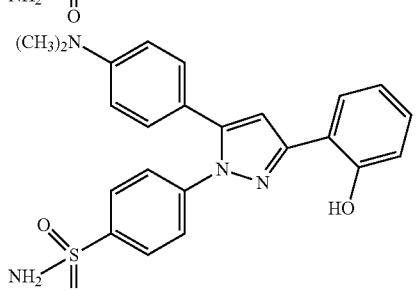
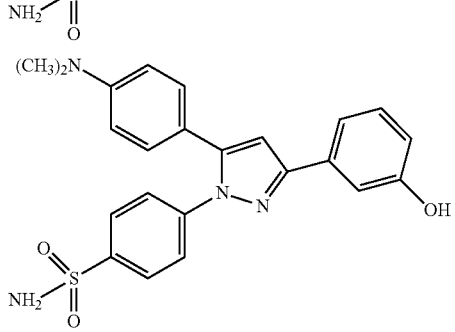
-continued
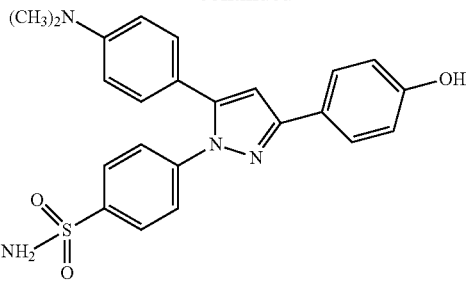
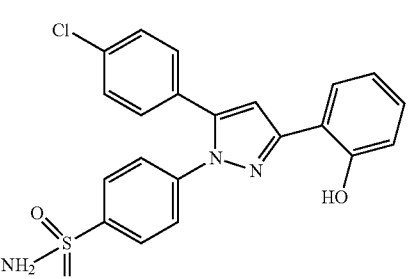
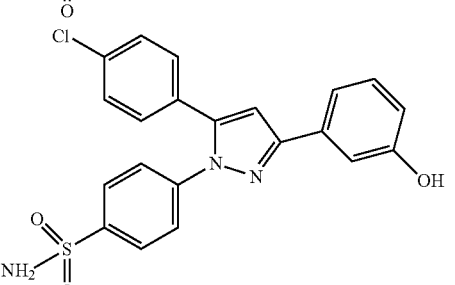
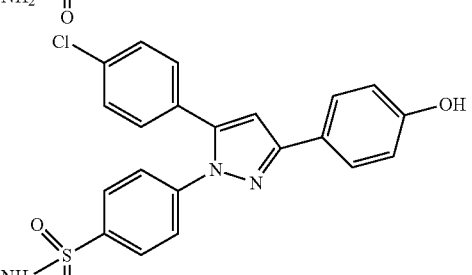
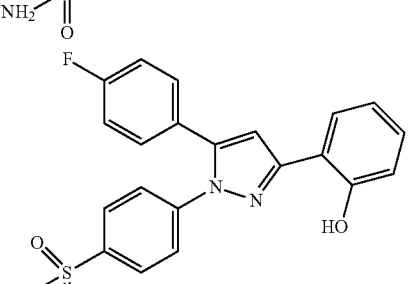
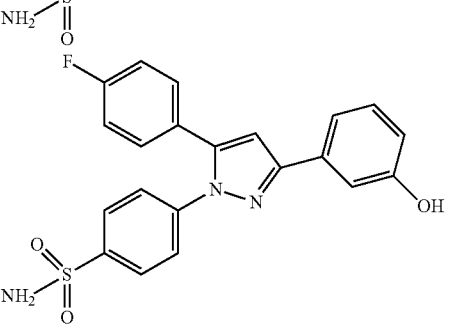

-continued
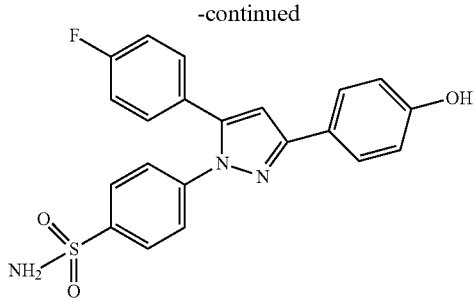
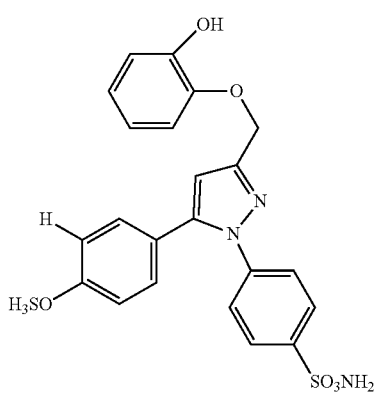
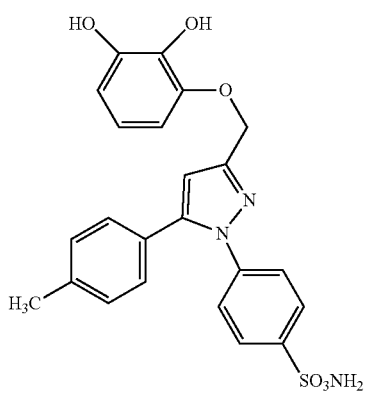
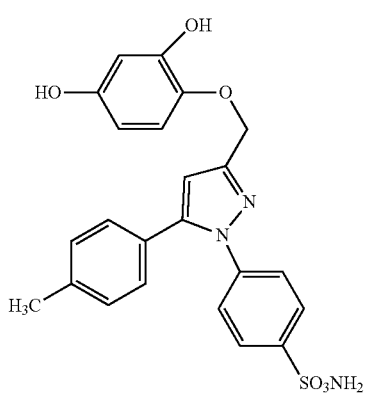
-continued
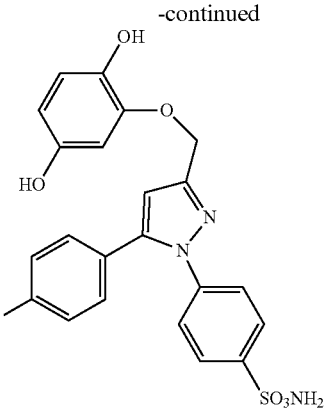
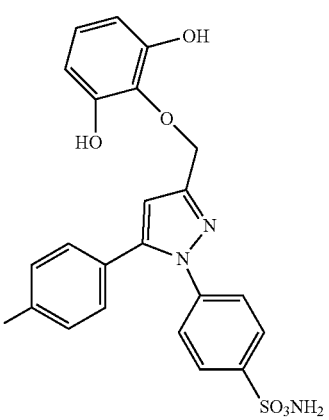
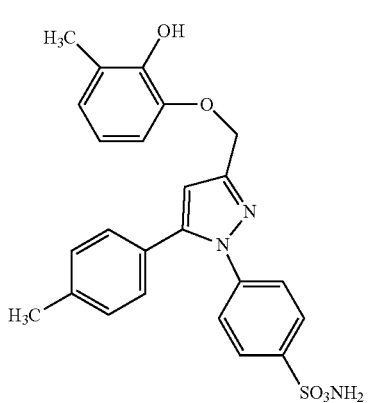
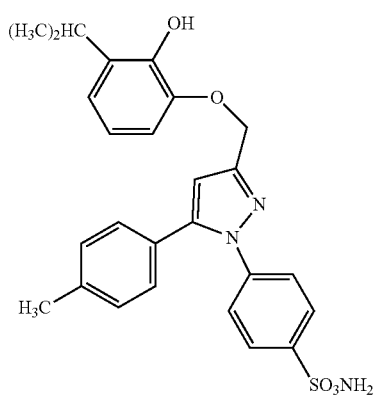

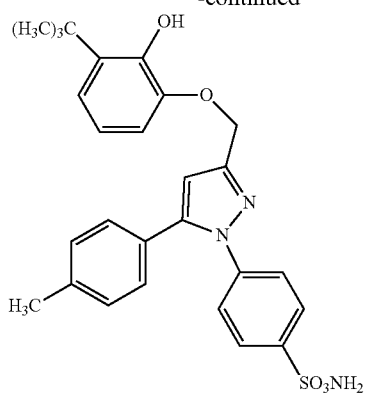
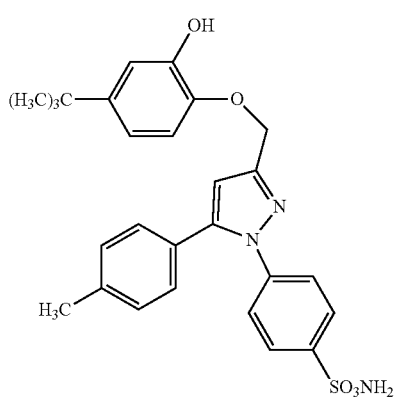
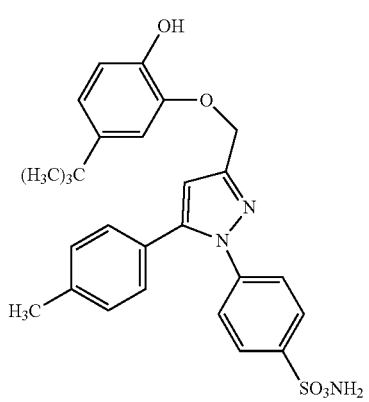
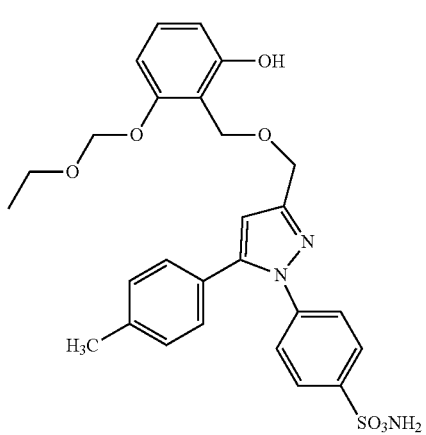
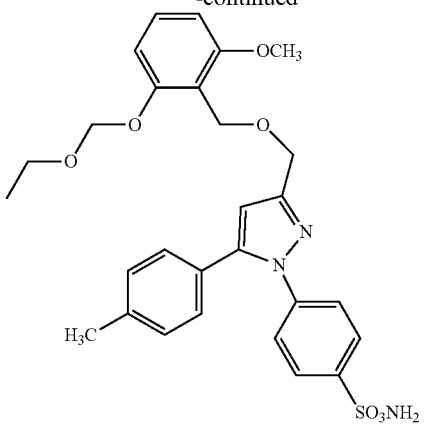
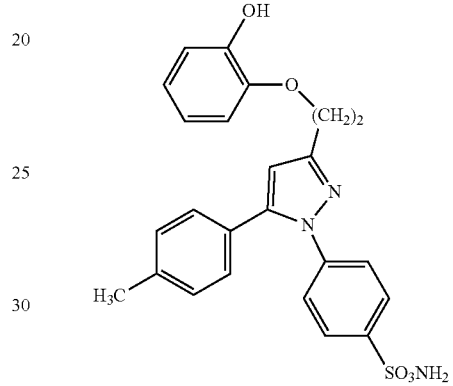
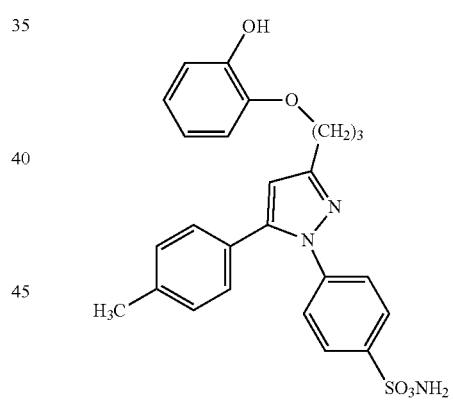
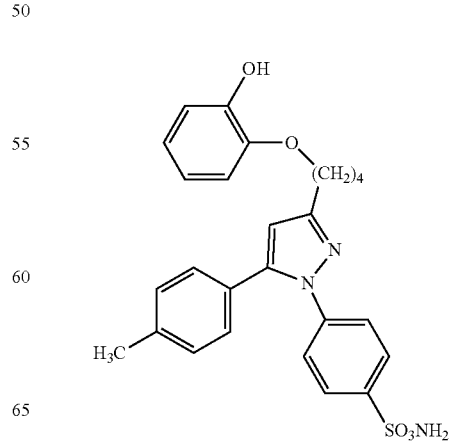

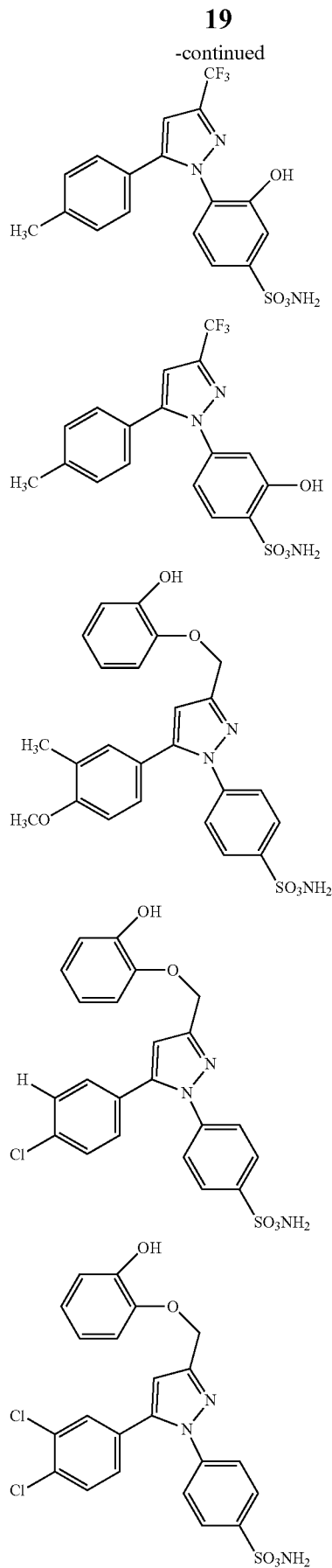

A typical synthesis scheme is listed in FIG. 1.
The second class of compounds is defined by formula 2.

(2)

wherein R₁ is selected from hydroxyl, amino, alkyl, carboxyalkyl, alkoxycarbon yl, aminocarbon yl, aminocarbonylalkyl, alkoxycarbonylalkyl, carboxyl, alkoxy, haloalkoxy, aralkoxy, heteroaralkoxy, cycloalkylalkoxy, alkylthio, aralkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, heterocyclo, heterocycloalkyl, aryl, aralkyl, halo, alkylamino, aralkylamino, N-alkyl-N-aralkylamino, heteroaralkylamino, N-alkyl-N-heteroaralkylamino, N-alkyl-N-cycloalkylalkylamino, arylcarbonylthio, alkylaminocarbonylthioalkyl, arylcarbonyloxyalkyl, alkoxycarbon yloxyalkyl, alkylaminocarbonyloxyalkyl, alkoxycarbonylthioalkyl, and alkylaminocarbonylthioalkyl when R₂ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

wherein R₂ is selected from cycloalkyl, cycloalkenyl, aryl and heterocyclo; wherein R₃ is optionally substituted at a substitutable position with one or more radicals independently selected from alkyl, cyano, carboxyl, alkoxycarbonyl, haloalkyl, hydroxyl, hydroxyalkyl, haloalkoxy, amino, aminoalkyl, alkylamino, arylamino, nitro, alkoxyalkyl, alkylsulfinyl, aminosulfonyl, halo, alkoxy and alkylthio when R₁ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

wherein R₃ is one or more radicals independently selected from alkyl, cyano, carboxyl, alkoxycarbonyl, haloalkyl, hydroxyl, hydroxyalkyl, haloalkoxy, amino, aminoalkyl, alkylamino, arylamino, nitro, alkoxyalkyl, alkylsulfinyl, halo, hydroxysulfonyl, alkylsulfonyl, aminosulfonyl, haloalkylsulfonyl, alkoxy and alkylthio; or a pharmaceutically-acceptable salt thereof.

A preferred class of compounds consists of those compounds of Formula 3 wherein R4 is sulfamyl or substituted sulfamyl, wherein R1 is from hydrido, halo, wherein R2 is selected from aryl with substitute of methyl, methoxyl, halo, hydrido, or methylthio and pharmaceutically acceptable salts thereof as follows:

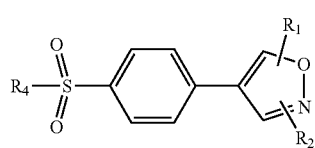

(3)

wherein R₁ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, heteroaralkoxy, cycloalkylalkoxy, alkylthio, aralkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, heterocyclo, heterocycloalkyl, aralkyl, halo, alkylamino, aralkylamino, N-alkyl-N-aralkylamino, heteroaralkylamino N-alkyl-N-hetero aralkylamino, N-alkyl-N-cycloalkylalkylamino, arylcarbonyloxy alkyl, arylcarbonylthio, alkoxyc arbonyloxyalkyl, alkylaminocarbonyloxyalkyl, alkoxycarbonylthioalkyl, and alkylaminocarbonylthioalkyl, when R₂ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

wherein R₄ is selected from alkyl, hydroxyl, and amino; peptides, or a pharmaceutically-acceptable salt thereof.

Within Formula 3, there is a subclass of compounds of high interest represented by Formula 4.

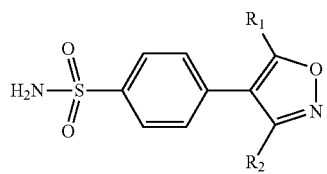

(4)

wherein R₁ is selected from hydroxyl, alkyl, carboxyalkyl, aminocarbonylalkyl, alkoxycarbonylalkyl, carboxyl. alkoxy, haloalkoxy, aralkoxy, heteroaralkoxy, cycloalkylalkoxy, alkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, heterocyclo, heterocycloalkyl, aralkyl, halo, alkylamino, aralkylamino, N-alkyl-N-aralkylamino, heteroaralkylamino, N-alkyl-N-heteroaralkylamino, alkyl-N-cycloalkylalkylamino, arylcarbonyloxy alkyl, arylcarbonylthio, alkoxycarbonyloxyalkyl, alkylaminocarbonyloxyalkyl, alkoxycarbonylthioalkyl, and alkylaminocarbonylthioalkyl when R₂ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

Or wherein R₂ is selected from hydroxyl, alkyl, carboxyalkyl, aminocarbonylalkyl, alkoxycarbonylalkyl, carboxyl. alkoxy, haloalkoxy, aralkoxy, heteroaralkoxy, cycloalkylalkoxy, alkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, heterocyclo, heterocycloalkyl, aralkyl, halo, alkylamino, aralkylamino, N-alkyl-N-aralkylamino, heteroaralkylamino, N-alkyl-N-heteroaralkylamino, alkyl-N-cycloalkylalkylamino, arylcarbonyloxy alkyl, arylcarbonylthio, alkoxycarbonyloxyalkyl, alkylaminocarbonyloxyalkyl, alkoxycarbonylthioalkyl, and alkylaminocarbonylthioalkyl when R₁ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

A preferred class of compounds (backbone in Formula 5) consists of those compounds of Formula (4) wherein R1 is selected from hydroxyl, lower alkyl, carboxyl, lower carboxyalkyl, lower aminocarbonylalkyl, lower alkoxycarbonylalkyl, lower aralkyl, lower alkoxyalkyl, lower aralkoxyalkyl, lower alkylthioalkyl, lower aralkylthioalkyl, lower alkylaminoalkyl, lower aryloxyalkyl, lower arylthioalkyl, lower haloalkyl, lower hydroxylalkyl, lower cycloalkyl, lower cycloalkylalkyl, and aralkyl when R2 is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.

Or wherein R₂ is optionally substituted at a substitutable position with one or more radicals independently selected from lower alkylsulfinyl, aminosulfonyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy and lower alkylthio; when R₁ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid, or a pharmaceutically-acceptable salt thereof or a pharmaceutically-acceptable salt thereof.

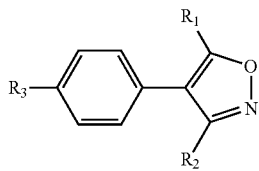
(5)

The third class of compounds are defined by Formula 6 or any pharmaceutically acceptable salts thereof.

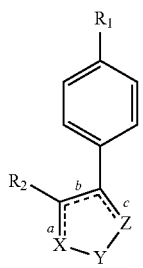
(6)

Wherein X—Y—Z is selected from the group consisting of
(a) —CH$_2$CH$_2$CH$_2$—
(b) —C(O)CH$_2$CH$_2$—
(c) —CH$_2$CH$_2$C(O)—
(d) —CR (R)—O—C(O)—
(e) —C(O)—O—CR$_5$(R$_{5'}$)
(f) —CH—NR$_3$—CH—
(g) —CR$_5$(R$_{5'}$)—NR$_3$—C(O)—,
(h) —CR$_4$=CR$_{4'}$—S—,
(i) —S—CR$_4$=CR$_{4'}$
(j) —S—N=CH—
(k) —CH=N—S—
(l) —N=CR$_4$—O—
(m) —O—CR$_4$=N—
(n) —N=CR$_4$—NH—
(o) —N=CR$_4$—S—,
(p) —S—CR$_4$—N—
(q) —C(O)—NR—CR (R')—
(r) —R$_3$N—CH=CH— provided R$_1$ is not —S
(s) —R$_3$N—CH=CH— provided R$_1$ is not —S(O) Me
With any Rx replaced in any place in above moiety. Wherein Rx is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid, or a pharmaceutically-acceptable salt thereof.
When side b is a double bond, and sides a and c are single bonds; and X—Y—Z—is selected from the group consisting of:
(a) =CH—O—CH=, and
(b) =CH—NR$_3$—CH—
(c) N—S—CH=
(d) =CH—S—N=
(e) N—O—CH=
(f) =CH—O—N=
(g) N—S—N=,
(h) —N—O—N=,
With any Rx replaced in any place in above moiety. Wherein Rx is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid, or a pharmaceutically-acceptable salt thereof.

When sides a and c are double bonds and side b is a single bond R$_1$ is selected from the group consisting of
(a) S(O)$_2$CH$_3$
(b) S(O)$_2$NH$_2$
(c) S(O)$_2$NHC(O)CF$_3$
(d) S(O)(NH)CH$_3$
(e) S(O)(NH)NH$_2$
(f) S(O)(NH)NHC(O)CF$_3$
(g) P(O)(CH$_3$)OH, and
(h) P(O)(CH$_3$)NH R$_2$ is selected from the group consisting of
(a) C$_{1-6}$alkyl
(b) C$_3$, C$_4$, C$_5$, C$_6$, and C$_7$ cycloalkyl
(c) mono-, di- or tri-substituted phenyl or naphthyl wherein the substituent is selected from the group consisting of
(1) hydrogen
(2) halo
(3) C$_{1-6}$ alkoxy
(4) C$_{1-6}$ alkylthio
(5) CN
(6) CF$_3$
(7) C$_{1-6}$ alkyl
(8) N3
(9) —CO$_2$H
(10) —CO$_2$—C$_{1-4}$alkyl
(11) —C(R$_5$)(R$_6$)—OH,
(12) —C(R$_5$)(R$_6$)—O—C$_{1-4}$alkyl,
(13) —C$_{1-6}$alkyl-CO2—R$_5$
(d) mono-, di-or tri-substituted heteroaryl wherein the heteroaryl is a monocyclic aromatic ting of 5 atoms, said ting having one hetero atom which is S, O, or N and optionally 1, 2, or 3 additionally N atoms; or the heteroaryl is a monocyclic ting of 6 atoms, said ring having one hetero atom which is N, and optionally 1, 2, 3, or 4 additional N atoms; said substituents are selected from the group of
(1) hydrogen
(2) halo, including fiuoro, chloro, bromo and iodo,
(3) C$_{1-6}$alkyl
(4) C$_{1-6}$alkoxy
(5) C$_{1-6}$alkylthio
(6) CN
(7) CF3
(8) N$_3$
(9) —C(R$_5$)(R$_6$)—OH, and
(10) —C(R$_5$)(R$_6$)—O—C$_{1-4}$alkyl
R$_3$ is selected from the group consisting of
(a) Hydrogen
(b) CF$_3$
(c) CN
(d) C$_{1-6}$alkyl,
(e) hydroxy C$_{1-6}$alkyl
(f) —C(O)—C$_{1-6}$ alkyl
(a) optionally substituted
(1) C1-salkyl-Q
(2) —C$_{1-3}$alkyl-O—C$_{1-3}$alkyl-Q
(3) —C$_{1-3}$alkyl-S—C$_{1-3}$alkyl-Q
(4) —C$_{1-5}$alkyl-O-Q
(5) —C$_{1-5}$alkyl-S-Q
R$_4$ and R$_{4'}$ are each independently selected from the group consisting of wherein the substituent resides on the alkyl and the substituent is $C_{1-3}$alky
(a) Hydrogen
(b) $CF_3$
(c) CN
(d) $C_{1-6}$alkyl
(e) —Q
(f) —O-Q
(g) —s-Q
(h) Optionally substituted
  (1) —$C_{1-5}$alkyl-Q,
  (2) —O—$C_{1-5}$alkyl-Q,
  (3)(3) —S—$C_{1-5}$alkyl-Q,
  (4)(4) —$C_{1-3}$alkyl-O—$C_{1-3}$alkyl-Q,
  (5)(5) —$C_{1-3}$alkyl-S—$C_{1-3}$alkyl-Q,
  (6) —$C_{1-5}$alkyl-O-Q,
  (7) —$C_{1-5}$ alkyl-S-Q wherein the substituent resides on the alkyl and the substituent is $C_{1-3}$alkyl, and $R_5$, $R_{5'}$, $R_6$, $R_7$ and $R_8$ are each independently selected from the group consisting of
(a) Hydrogen
(b) $C_{1-6}$ alkyl
Or $R_5$ and $R_6$ and $R_7$ and $R_8$ together with the carbon to which they are attached from a saturate monocyclinc carbon ring of 3, 4, 5, 6, or 7 atoms;
Q is COOH, COO—$C_{1-4}$alkyl, tetrazoly-5-yl, $C(R_7)(R_8)$(OH) or $C(R_7)(R_8)(O_{1-4}alkyl)$ provided that when X—Y—Z is S—$CR_4$=$CR_{4'}$, then $R_4$ and $R_{4'}$ are other than $CF_3$—

A preferred class of compounds (In formula 7) consists of those compounds of Formula 6 wherein R1 is sulfamyl or substituted sulfamyl, wherein R2 is selected from from hydroxyl, alkyl, carboxyalkyl, aminocarbonylalkyl, alkoxycarbonylalkyl, carboxyl. alkoxy, haloalkoxy, aralkoxy, heteroaralkoxy, cycloalkylalkoxy, alkylthio, heteroaralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyalkyl, haloalkyl, cycloalkyl, cycloalkylalkyl, heterocycloalkyl, heterocycloalkyl, aralkyl, halo, alkylamino, aralkylamino, N-alkyl-N-aralkylamino, heteroaralkylamino, N-alkyl-N-heteroaralkylamino, alkyl-N-cycloalkylalkylamino, arylcarbonyloxy alkyl, arylcarbonylthio, alkoxycarbonyloxyalkyl, alkylaminocarbonyloxyalkyl, alkoxycarbonylthioalkyl, and alkylaminocarbonylthioalkyl.
wherein $R_3$ is from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid, or a pharmaceutically-acceptable salt thereof.

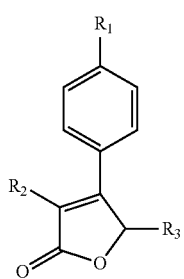

(7)

The fourth class of compounds are defined by Formula 8 or any pharmaceutically acceptable salts thereof.

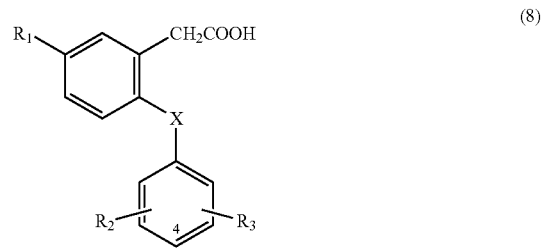

(8)

wherein $R_1$ is selected from methyl, ethyl, or any other alkyl
wherein $R_2$ is selected from halo, hydrogen, methoxyl, methyl, ethyl, trifluoromethyl when $R_3$ is hydroxyl (exclude position-4).
Wherein X is selected from N, O, C.

The fifth class of compounds are defined by Formula 9 or any pharmaceutically acceptable salts thereof.

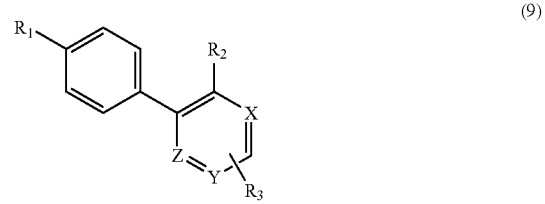

(9)

Wherein $R_1$ is selected from sulfamyl, substituted sulfamyl, halo, alkyl, alkoxy, hydroxyl, and haloalkyl.
wherein $R_2$ is selected from hydrido, halo, haloalkyl, cyano, nitro, formyl, carboxyl, alkoxycarbonyl, carboxyalkyl, alkoxycarbonylalkyl, amidino, cyanoamidino, arnido, alkoxy, amidoalkyl, N-monoalkylamido, N-monoarylamido, N,N-dialkyla-mido, N-alkyl-N-arylamido, alkylcarbonyl, alkylcarbo-nylalkyl, hydroxyalkyl, alkylthio, alkylsulfinyl, alkyl-sulfonyl, N-alkylsulfamyl, N-arylsulfamyl, arylsulfonyl, N,N-dialkylsulfamyl, N-alkyl-N-arylsulfamyl, and heterocyclic
wherein $R_3$ is selected from any aromatic moiety, such as phenyl, pyridyl, thienyl, oxazolyl, isoxazolyl, benzoxazolyl, thiazolyl, quinolinol, pyridinol, with one or more hydroxyl(s) or with one or more amine(s) that can be conjugated with glucuronic acid or sulphonic acid.
Wherein X, Y, Z is selected from N and C.

By integrating all of the results disclosed herein with respect to the activities, absorption, metabolism, excretion and systemic bioavailability of 6a1 in rats, only less than 1% of 6a1 absorbed in the colon escaped the first-pass metabolism in the liver. Thus, when 6a1 or other locally bioavailable COX-2 inhibitors are developed as novel agents to treat colonic inflammatory diseases or prevent CRC in patients, a much higher safety index for the cardiovascular system can be expected than that of celecoxib.

EXAMPLES

Experiment 1

Figure 2A:
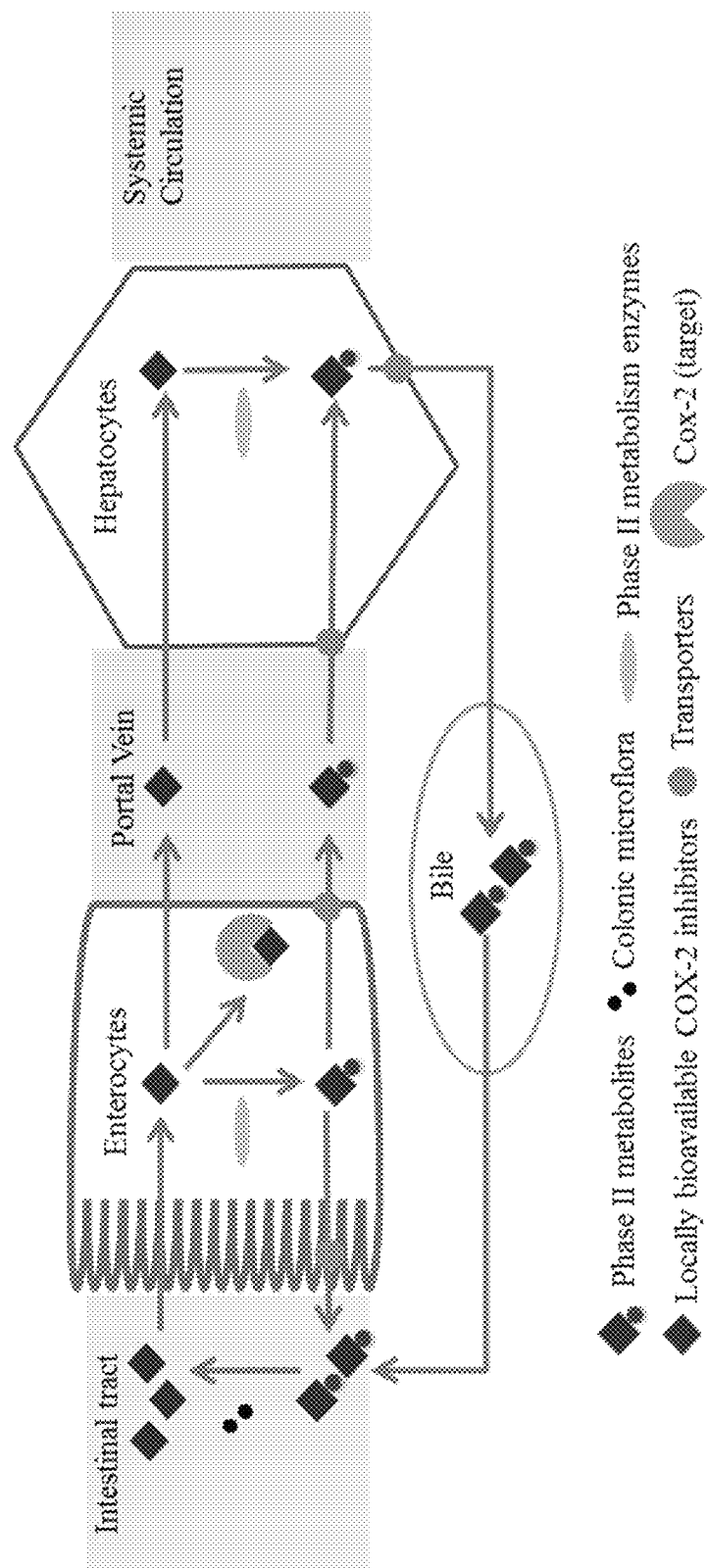
FIG. 2A is an illustration of the absorption, metabolism, excretion, hydrolysis and reabsorption of the locally bioavailable COX-2 inhibitors in the colonic epithelium and liver.
Figure 2B:
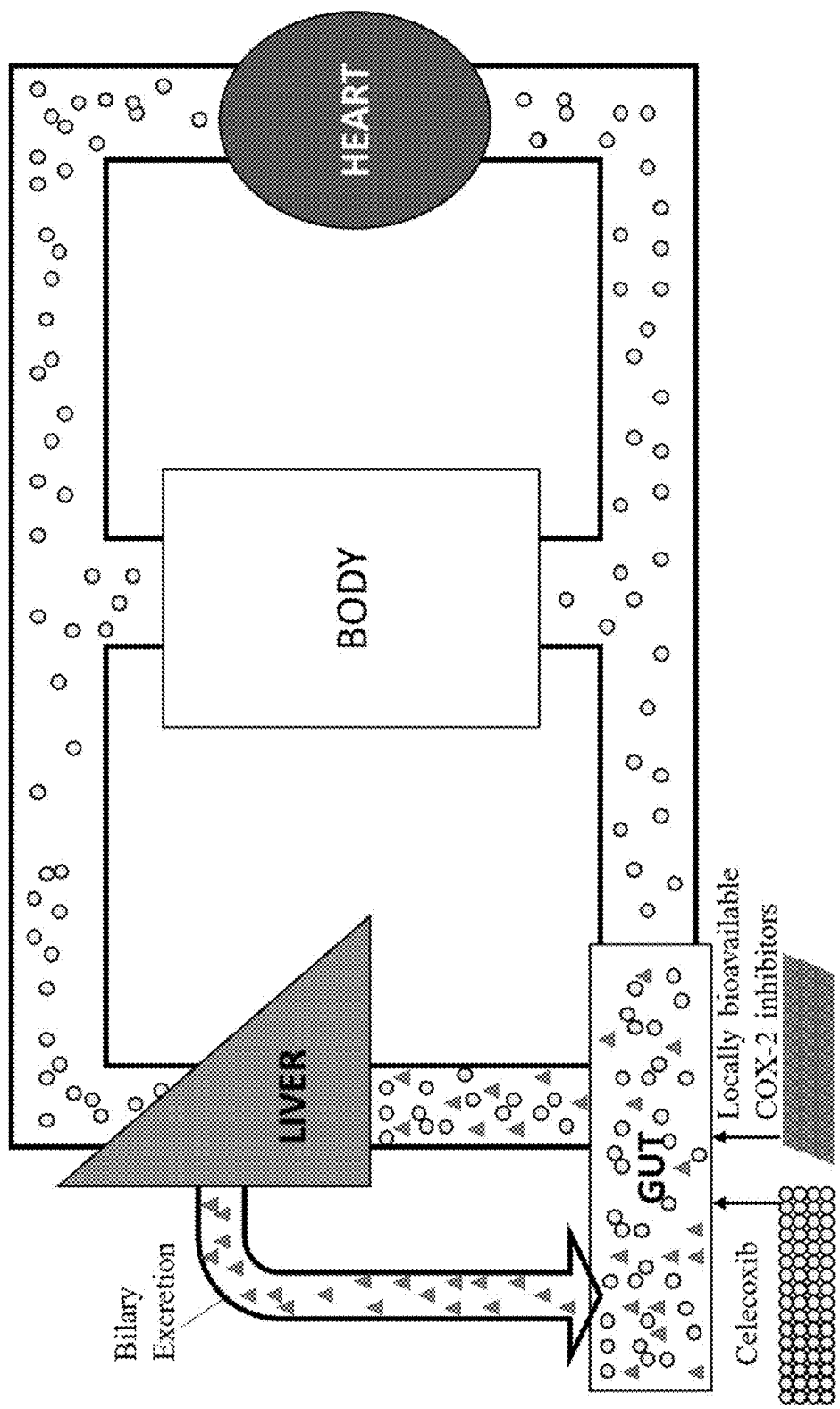
FIG. 2B is a comparison of the pharmacokinetic properties between celecoxib and the locally bioavailable COX-2 inhibitors in the human body after administration. The distribution of the locally bioavailable COX-2 inhibitors and their metabolites are limited to the gut and liver due to the extensive first-pass metabolism and enterohepatic circulation. The high concentration of celecoxib in the systemic circulation increases the risk of cardiovascular events in patients.

Design and Synthesis of Lead Compounds for Locally Active and Systemically Unavailable or Minimally Available COX-2 Inhibitors for Colonic Diseases In an embodiment, new compounds (FIG. 1), are built with phenolic hydroxyl groups that are highly susceptible to glucuronidation and or sulfonation in their structures, which is quite different from celecoxib and the other current COX-2 inhibitors. As potent COX-2 inhibitors, these compounds inhibit colonic COX-2 activity and are locally active when a high enough concentration is achieved in the colonic lumen and colon tissue after administration of drugs formulated to release the drugs in the colon (FIG. 2A). The purposefully designed phenolic groups can be efficiently conjugated by the human phase II metabolic enzymes, i.e., they are inactivated by the first-pass metabolism, mainly UGTs and SULTs [11, 12]. Because UGTs and SULTs are abundantly expressed in the human liver but not highly expressed in the colon, the COX-2 inhibitors with phenolic groups in the structure can be extensively metabolized in the liver (i.e., high first-pass metabolism) before they can enter the systemic circulation (FIG. 2A). Thus, the locally bioavailable COX-2 inhibitors and their metabolites, mainly glucuronides and sulfates, are prevented from entering the systemic circulation, and thus do not cause cardiovascular toxicity (FIG. 2B). The phase II metabolism is employed for this purpose because the metabolic rates of phenolic compounds by UGTs and SULTs can occur much more rapidly than those in phase I metabolism by cytochrome P450 (CYP450s). More importantly, these metabolites can reproduce active COX-2 inhibitors in the colon via enterohepatic recycling or recirculation. Enterohepatic recycling is a process where microbial hydrolysis of a drug's glucuronides and sulfates excreted through the bile, will reproduce the active compounds that can be present in and absorbed from the colon. Hence, utilizing enterohepatic recycling will increase the drug concentrations and residence times in the colon without increasing systemic drug concentrations. The enterohepatic recirculation of the locally bioavailable COX-2 inhibitors will prolong the duration of their efficacies in the colon (FIG. 2A and FIG. 2B).

Example 2

$IC_{50}$ Values of the Newly Synthesized COX-2 Inhibitors

The inhibitory activity on COX-2 is successfully retained after metabolically labile motifs are built into the active COX-2 inhibitors. First, the inhibitory effects of the new synthesized compounds on COX-2 were assayed in two cell lines: Raw264.7 cells and HCA-7 cells. Raw264.7 is a mouse macrophage cell line which expresses a high level of COX-2 protein upon lipopolysaccharide (LPS) induction. The cells were co-incubated for 14 hours with 0.1 μg/mL LPS and different concentrations of the new compounds. The concentration of prostaglandins (both PGD2 and PGE2) accumulated in the cell culture medium can be employed as an indicator of COX-2 activity. HCA-7 is a human colon cancer cell line in which COX-2 protein is constitutively expressed. Briefly, the cells were pre-incubated with different concentrations of the new compounds for 30 min, and then 10 μM A23187 (a calcium ionophore) was added to release membrane-bound arachidonic acid (the natural substrate of COX-2) to the cytosolic domain. The system was incubated for another 30 minutes and PGE2 concentrations in the culture medium were determined. In both cell lines, higher PGD2/PGE2 concentrations in the media meant more COX-2 activity.

The IC50 values of the newly synthesized compounds on COX-2 activity in the two cell lines are shown in Table 1. Although not as potent as celecoxib (the positive control), the new compounds still can inhibit COX-2 efficiently at concentrations that are locally achievable in the colon (≤1 μM). IC50s for 6a1-4 on COX-2 were observed to be comparable to each other in HCA-7 cells. However, in Raw264.7 cells 6a1 and 6a2 were far less potent than the other two. The divergence appears to be due to the differences between the cell lines and the different experimental protocols used.

TABLE 1

$IC_{50}$s of celecoxib and new compounds on COX-2 activity in Raw264.7 cells and HCA-7 cells

| Compound | M.W. | LogP | $IC_{50}$ (μM) on mouse COX-2 in Raw264.7 cells | $IC_{50}$ (μM) on human COX-2 in HCA-7 cells |
|---|---|---|---|---|
| 6a1 | 435.1 | 4.64$^a$ | 1.387 ± 0.384 | 0.195 ± 0.030 |
| 6a2 | 435.1 | 4.64$^a$ | 4.618 ± 1.342 | 0.134 ± 0.018 |
| 6a3 | 435.1 | 4.64$^a$ | 0.019 ± 0.002 | 0.064 ± 0.005 |
| 6a4 | 579.6 | 4.90$^a$ | 0.303 ± 0.055 | 0.162 ± 0.065 |
| 6b2 | 421.5 | 4.15$^a$ | 4.311 ± 0.629 | ND |
| 6b3 | 421.5 | 4.15$^a$ | 0.033 ± 0.004 | ND |
| 6c2 | 451.1 | 4.02$^a$ | 2.379 ± 0.502 | ND |
| 6c3 | 451.1 | 4.02$^a$ | 0.019 ± 0.002 | ND |
| 3a | 385.1 | 3.58$^a$ | 0.071 ± 0.021 | 0.149 ± 0.026 |
| Celecoxib | 381.4 | 4.01$^b$ | 0.003 ± 0.001 | 0.003 ± 0.001 |

M.W., Molecular Weight.
ND, Not Determined.
$^a$predicted with ChemDraw Software.
$^b$from http://www.drugbank.ca/drugs/DB00482

Figure 3A:
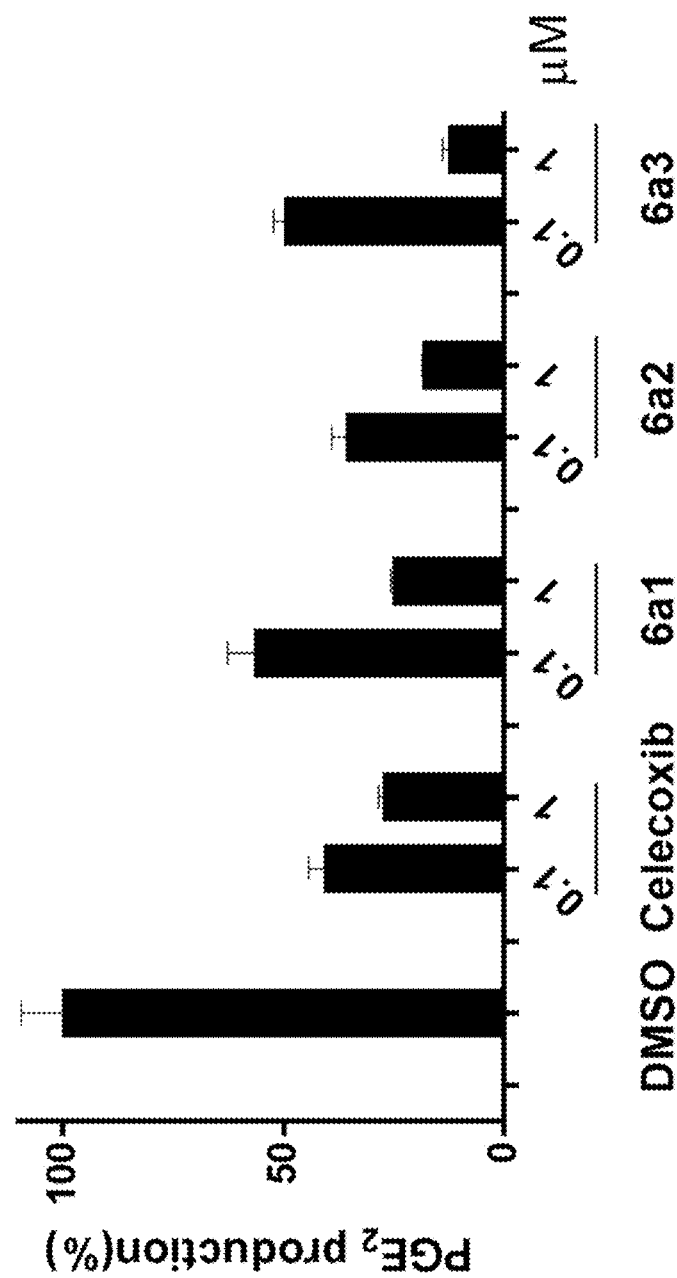
FIG. 3A is a bar graph illustration of PGE2 production by recombinant human COX-2 enzyme in the presence of the new compounds. Less PGE2 production means inhibition of COX-2 enzyme. More potent inhibitors are able to inhibit PGE2 production at lower inhibitor concentration. This figures showed that 6a1, 6a2, and 6a3 were effective inhibitors of COX-2 enzyme.
Figure 3B:
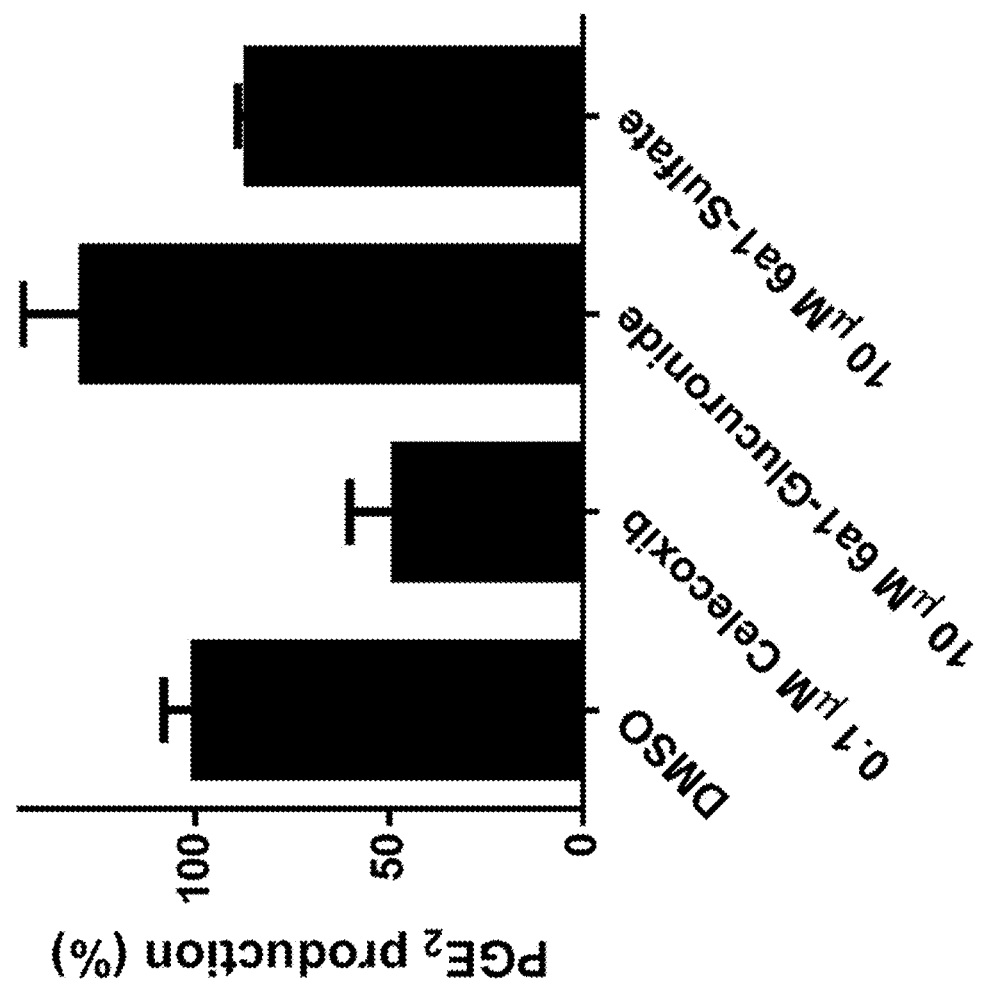
FIG. 3B is a bar graph illustration of PGE2 production by recombinant human COX-2 enzyme in the presence of the metabolites of the new compounds. Less PGE2 production means inhibition of COX-2 enzyme. This figure shows that phase II conjugates of 6a1 were not inhibitors of COX-2 enzyme.

Next, the inhibitory effects of these phenolics against COX-2 and COX-1 were confirmed in an in vitro enzyme assay using recombinant human COX-2/1 (FIG. 3A). For example, 1 μM of 6a1-3 was found to inhibit COX-2 activity substantially (much more than 50%), while 0.1 μM of each was able to reduce PGE2 production by approximately 50%. Additionally, in this assay, the phase II metabolites of 6a1 (glucuronides and sulfates) produced by rat liver microsomes or S9 fractions were found to be inactive in inhibiting human recombinant COX-2 at a concentration as high as 10 μM (FIG. 3B). The results are listed in Table 2. The IC50 values and the ratios of COX-1 vs. COX-2, which indicate the gastrointestinal tract safety of 6c1, 7a1, and 7a3 are compatible to those of celecoxib, whose IC50 values against COX-1 and COX-2 were also listed in the table. However, the newly synthesized compounds are heavily metabolized in the human and rat liver microsomes (see below) and therefore are likely to be much safer to the cardiovascular system than celecoxib.

TABLE 2

$IC_{50}$ values against recombinant human COX2/1 (μM)

| Compounds | COX-2 | COX-1 | Ratio of COX-2/COX-1 |
|---|---|---|---|
| 6a1 | 0.1178 | 5.129 | 43.54 |
| 6a2 | 0.2012 | 27.23 | 135.34 |
| 6a3 | 1.077 | 38.25 | 35.52 |
| 6a4 | 2.592 | 15.95 | 6.15 |
| 6b1 | 54.52 | 196.8 | 3.61 |
| 6b2 | 0.2073 | 144.8 | 698.50 |
| 6b3 | 2.253 | 0.02805 | 0.01 |
| 6c1 | 0.04031 | 19.82 | 491.69 |
| 6c2 | 0.3592 | 1.104 | 3.13 |
| 6c3 | 0.6229 | 12.56 | 20.16 |
| 7a1 | 0.001108 | 4.904 | 4425.99 |
| 7a3 | 0.04031 | 19.8 | 491.19 |
| Celecoxib | 0.014 | 13.2 | 942.86 |

Example 3

Metabolism of the Locally Bioavailable COX-2 Inhibitors by Raw264.7 Cells

Figure 4A:
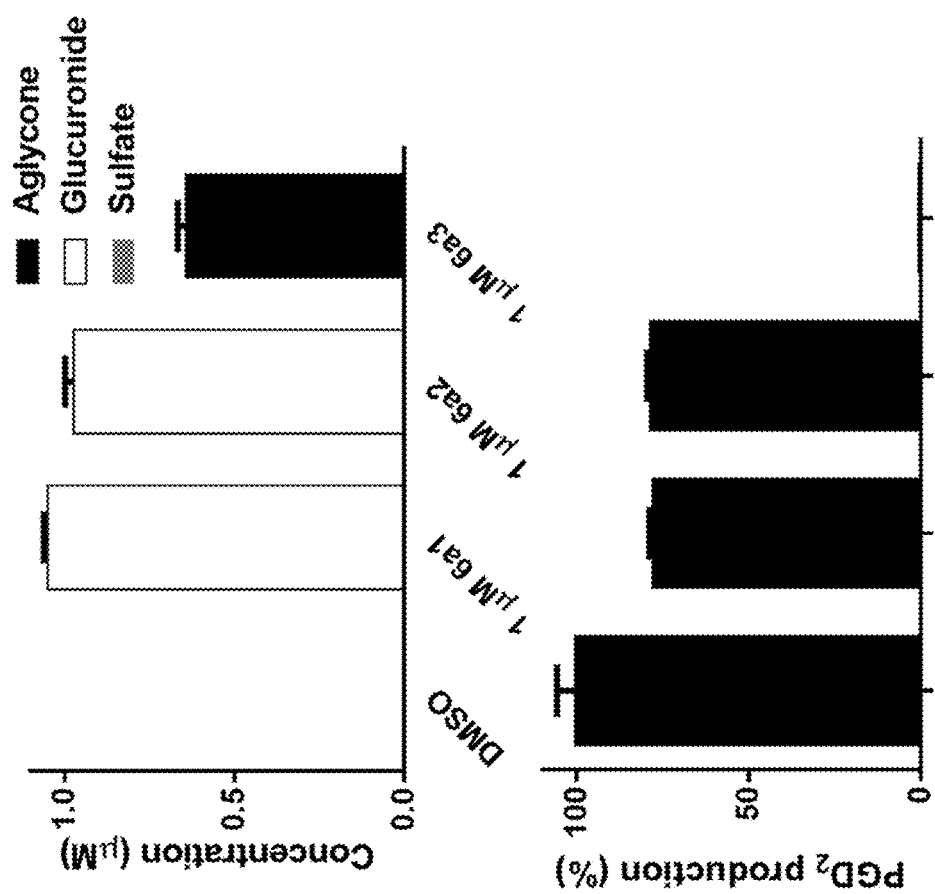
FIG. 4A is a bar graph illustration of the metabolism of the phenolics by Raw264.7 cells. Raw264.7 cells were incubated with 0.1 μg/mL LPS and 1 μM 6a1, 6a2 or 6a3, respectively. 14 hours later the concentrations of PGD2, the phenolics (i.e., aglycones, solid bars), and their phase II metabolites (open bars for glucuronides and shade bars for sulfates) were determined in the medium. Less PGD2 production means inhibition of COX-2 enzyme. This figure shows 6a1 and 6a2 were less effective than 6a3 because of phase II metabolism differences (i.e., more phase II metabolism means less activities in Raw264.7 cells).
Figure 4B:
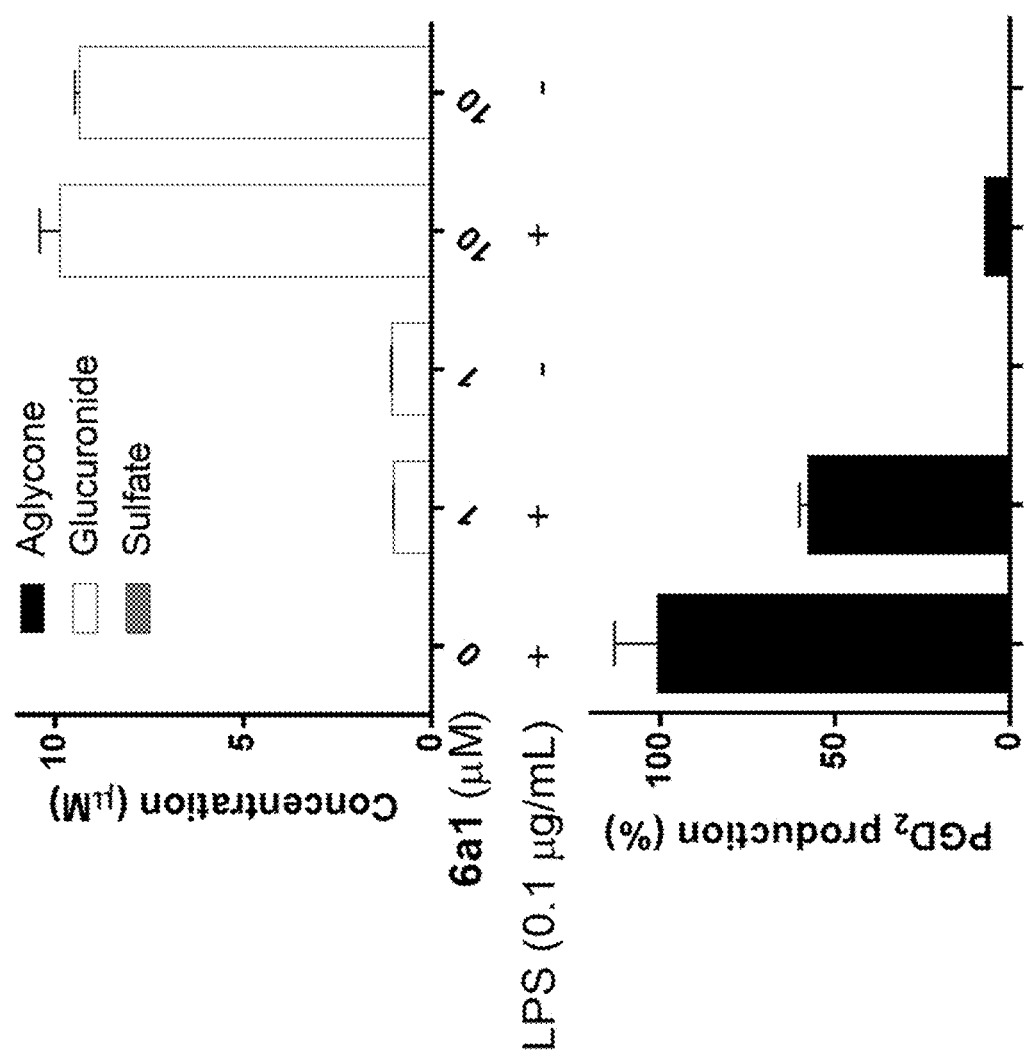
FIG. 4B is a bar graph illustration of the metabolism of the phenolics by Raw264.7 cells. Raw264.7 cells were incubated with different concentrations of 6a1 and LPS. 14 hours later the concentrations of PGD2, 6a1, and its metabolites were determined in the medium. Less PGD2 production means inhibition of COX-2 enzyme. This figure shows that higher concentration of 6a1 was more effective than lower concentration of 6a1.
Figure 4C:
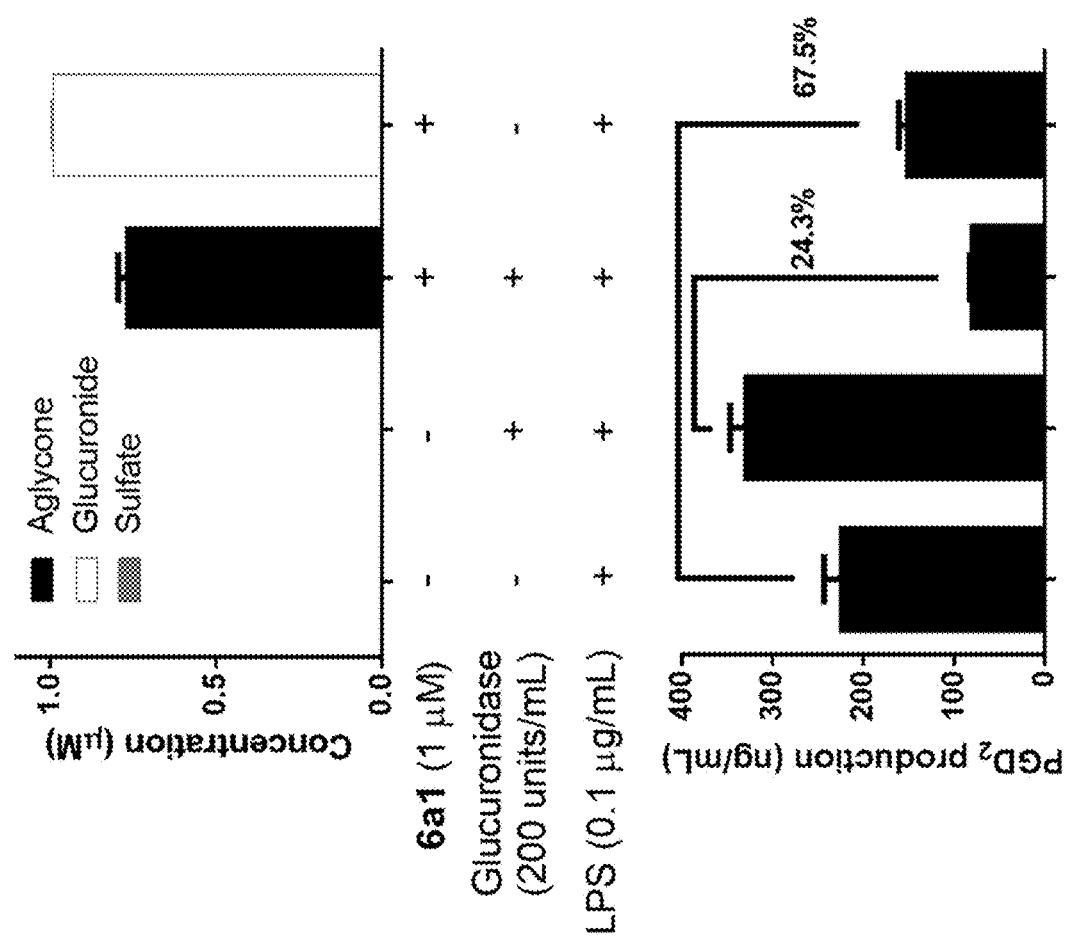
FIG. 4C is a bar graph illustration of the metabolism of the phenolics by Raw264.7 cells. Raw264.7 cells were incubated with 1 µM 6a1 and/or 200 units/mL β-glucuronidase. LPS (0.1 µg/mL) was also incorporated to induce COX-2 expression. 14 hours later the concentrations of PGD2, 6a1, and its metabolites were determined in the medium. Less PGD2 production means inhibition of COX-2 enzyme. This figure shows that in the presence of β-glucuronidase, which reconverted inactive 6a1 glucuronide to 6a1, increased aglycone concentration and resulted in more inhibition of the COX-2 enzyme.

To investigate why 6a1 and 6a2 were less potent than 6a3 in inhibiting COX-2 in Raw264.7 cells, Raw264.7 cells were co-incubated for 14 hours with 0.1 μg/mL and each of 6a1, 6a2, and 6a3 at 1 μM. The results indicated that at the end of the 14 hours incubation period, 6a1 and 6a2 were recovered exclusively as their glucuronides, while the majority of 6a3 stayed as aglycone (FIG. 4A, upper panel). Meanwhile, PGD2 production by the cells incubated with 1 μM 6a1 or 6a2 was only slightly reduced, while 1 μM 6a3 thoroughly inhibited PGD2 production (FIG. 4A, lower). Glucuronidation of 6a1 in Raw264.7 cells was not influenced by LPS (FIG. 4B). After glucuronidase was introduced into the cell culture system, 6a1 in the culture medium was recovered as aglycone and the inhibitory effects of 6a1 on PGD2 production was largely restored (24.3% of control with glucuronidase versus 67.5% of control without glucuronidase) (FIG. 4C). The results of these experiments initially indicate that when characterizing inhibitory effects of the phenolics on COX-2, the importance of metabolic stability should be brought into consideration. This could be why phenolics were not considered to be active against COX-2 in many published reports using cellular COX-2 assays. Hence, when phenolic compounds are employed as COX-2 inhibitors in the colon, an organ with metabolic enzyme expression, multiple factors must be considered to arrive at the best design.

Example 4

Metabolism of the Phenolics Characterized by in Vitro Tools

In vitro tools were employed to help predict the in vivo metabolism rates of the COX-2 inhibitors that are phenolics. The microsomes and S9 fractions prepared from colon or liver were used to determine the in vivo glucuronidation and sulfation rates of the phenolic compounds, respectively. By employing microsomes and S9 fractions prepared from both rats and humans, it could be determined if the results obtained in the rat model could be reasonably extrapolated to humans. In these experiments, raloxifene and genistein, two phenolic compounds which undergo extensive first-pass metabolism, were selected as controls [13, 14].

Figure 5A:
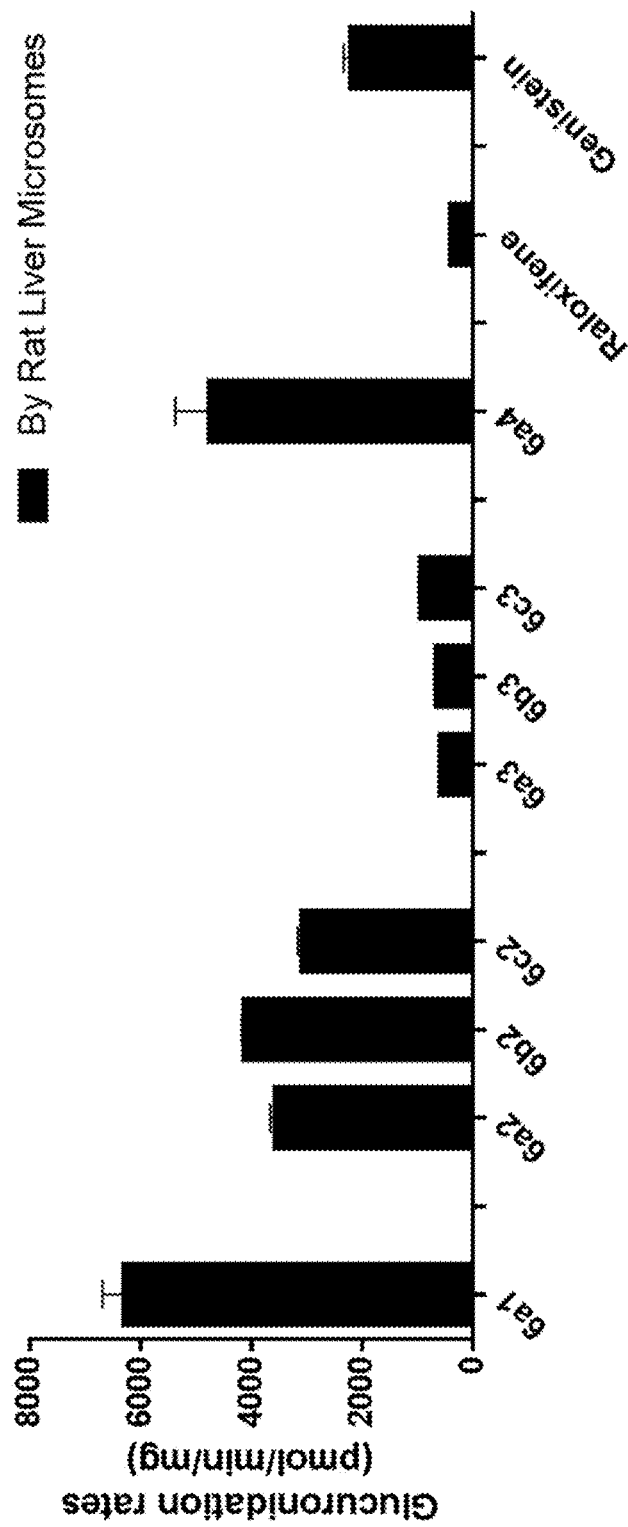
FIG. 5A is a bar graph illustrating in vitro metabolism of phenolics via glucuronidation pathway. Glucuronidation rates of all the new locally bioavailable COX-2 inhibitors by rat liver microsomes. Additional metabolic rates of various locally bioavailable COX-2 inhibitors are in Table 3. The in vitro metabolism rates were determined with a substrate concentration of 10 µM. Raloxifene and genistein are two compounds whose systemic bioavailability is less than 10% due to extensive glucuronidation and significant sulfonation. The incubation systems were: for glucuronidation, 0.88 mM magnesium chloride (MgCl2), 4.4 mM saccharolactone, 0.022 mg/mL alamethicin, 3.5 mM uridine 5'-diphospho-glucuronic acid (UDPGA), 10 µM substrates and different concentrations of microsomes in 50 mM potassium phosphate buffer (pH 7.4); for sulfation, 10 mM dithiothreitol (DTT), 5 mM MgCl2, 100 µM 3'-phosphoadenosine-5'-phosphosulfate (PAPS),10 µM substrate and different concentrations of S9 fractions in 50 mM potassium phosphate buffer (pH 7.4). This figure shows that 6a1, 6a2 and 6a4 were rapidly glucuronidated.
Figure 5B:
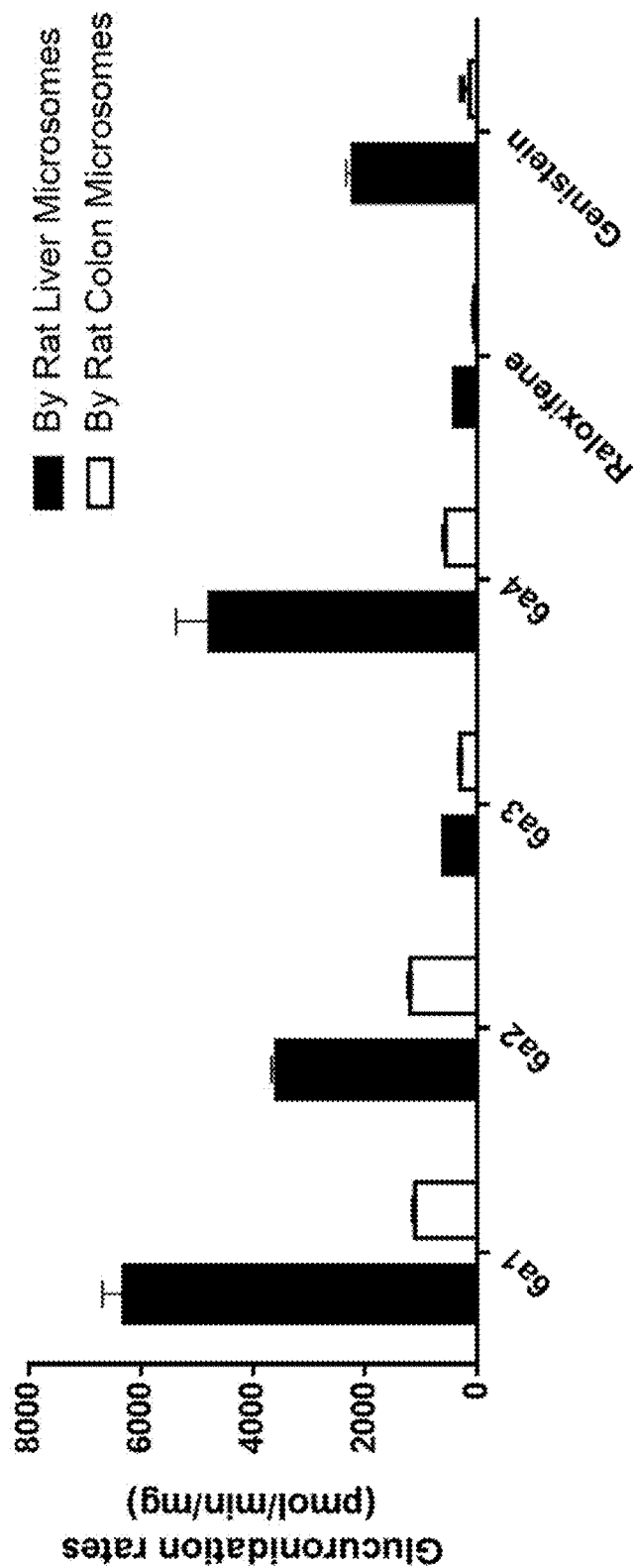
FIG. 5B is a bar graph illustrating in vitro glucuronidation of phenolics in liver and colon microsomes of rats. Glucuronidation rates of 6a1-6a4 by rat liver and colon microsomes were measured. Additional metabolic rates of various locally bioavailable COX-2 inhibitors are in Table 3. The in vitro metabolism rates were determined with a substrate concentration of 10 µM. Raloxifene and genistein are two compounds whose systemic bioavailability is less than 10% due to extensive glucuronidation and significant sulfonation. The incubation systems were: for glucuronidation, 0.88 mM magnesium chloride (MgCl2), 4.4 mM saccharolactone, 0.022 mg/mL alamethicin, 3.5 mM uridine 5'-diphospho-glucuronic acid (UDPGA), 10 µM substrates and different concentrations of microsomes in 50 mM potassium phosphate buffer (pH 7.4); for sulfation, 10 mM dithiothreitol (DTT), 5 mM MgCl2, 100 µM 3'-phosphoadenosine-5'-phosphosulfate (PAPS), 10 µM substrate and different concentrations of S9 fractions in 50 mM potassium phosphate buffer (pH 7.4). This figure shows that 6a1, 6a2 and 6a4 were much more rapidly glucuronidated in liver microsomes than colon microsomes, a desirable metabolic characteristic for locally bioavailable COX-2 inhibitors that will be effective in colon but not bioavailable systemically.
Figure 5C:
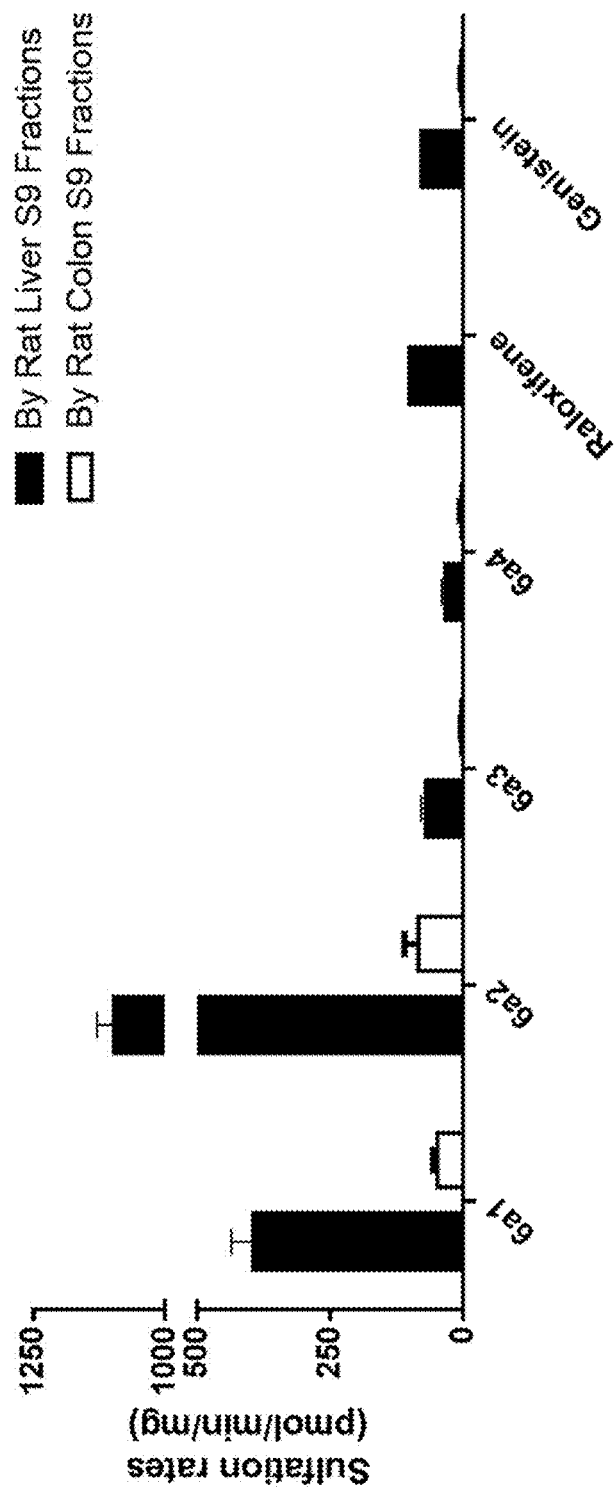
FIG. 5C is a bar graph illustrating in vitro metabolism of phenolics via sulfonation pathway. Sulfation rates of 6a1-6a4 by rat liver and colon S9 fractions. Additional metabolic rates of various locally bioavailable COX-2 inhibitors are in Table 3. The in vitro metabolism rates were determined with a substrate concentration of 10 µM. Raloxifene and genistein are two compounds whose systemic bioavailability is less than 10% due to extensive glucuronidation and significant sulfonation. The incubation systems were: for glucuronidation, 0.88 mM magnesium chloride (MgCl2), 4.4 mM saccharolactone, 0.022 mg/mL alamethicin, 3.5 mM uridine 5'-diphospho-glucuronic acid (UDPGA), 10 µM substrates and different concentrations of microsomes in 50 mM potassium phosphate buffer (pH 7.4); for sulfation, 10 mM dithiothreitol (DTT), 5 mM MgCl2, 100 µM 3'-phosphoadeno sine-5'-phosphosulfate (PAPS),10 µM substrate and different concentrations of S9 fractions in 50 mM potassium phosphate buffer (pH 7.4). This figure shows that 6a1, 6a2 and 6a4 were much more rapidly sulfonated in liver S9 fraction than colon S9 fraction, a desirable metabolic characteristic for locally bioavailable COX-2 inhibitors that will be effective in colon but not bioavailable systemically.
Figure 5D:
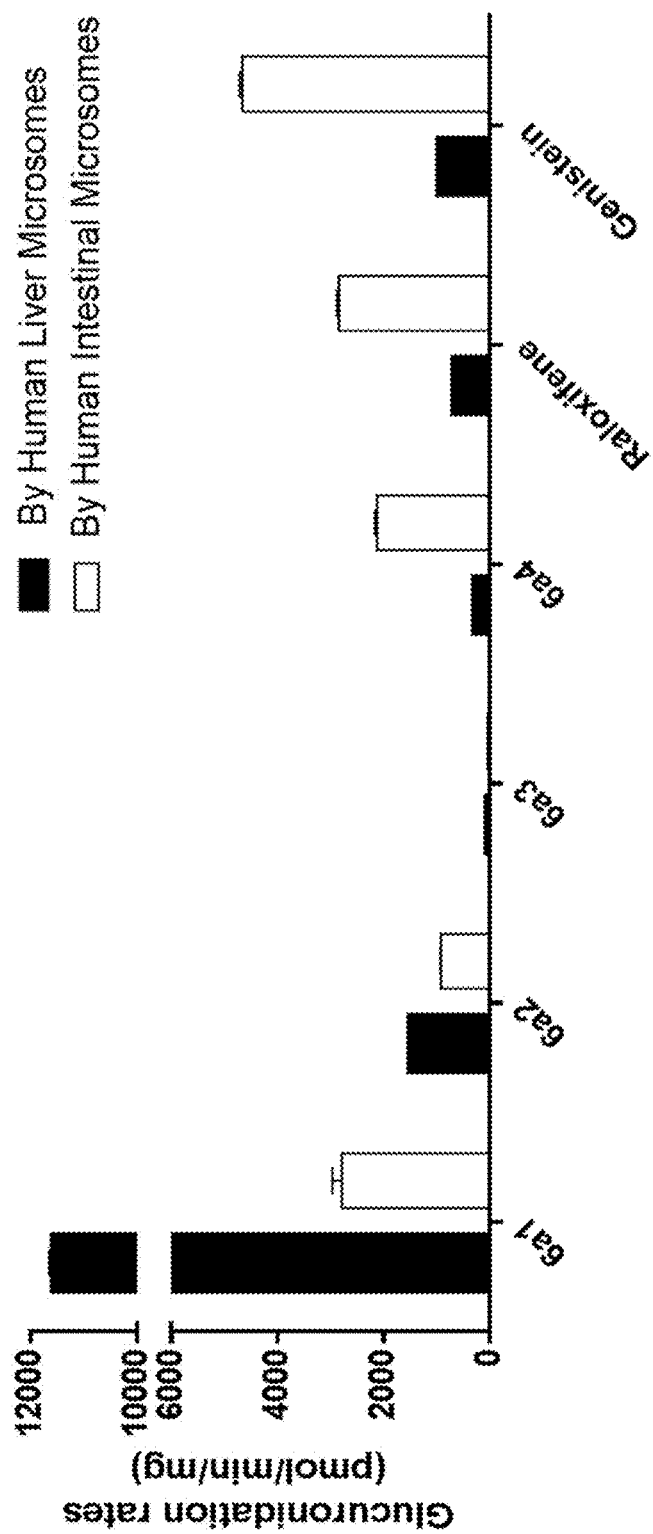
FIG. 5D is a bar graph illustrating in vitro metabolism of phenolics. Glucuronidation rates of 6a1-6a4 by human liver and intestinal microsomes. Additional metabolic rates of various locally bioavailable COX-2 inhibitors are in Table 4. The in vitro metabolism rates were determined with a substrate concentration of 10 µM. Raloxifene and genistein are two compounds whose systemic bioavailability is less than 10% due to extensive glucuronidation and significant sulfonation. The incubation systems were: for glucuronidation, 0.88 mM magnesium chloride (MgCl2), 4.4 mM saccharolactone, 0.022 mg/mL alamethicin, 3.5 mM uridine 5'-diphospho-glucuronic acid (UDPGA), 10 µM substrates and different concentrations of microsomes in 50 mM potassium phosphate buffer (pH 7.4); for sulfation, 10 mM dithiothreitol (DTT), 5 mM MgCl2, 100 µM 3'-phosphoadenosine-5'-phosphosulfate (PAPS),10 µM substrate and different concentrations of S9 fractions in 50 mM potassium phosphate buffer (pH 7.4). This figure shows that 6a1 was much more rapidly glucuronidated in liver microsomes than intestinal microsomes, a desirable metabolic characteristic for locally bioavailable COX-2 inhibitors that will be effective in colon but not bioavailable systemically. Compounds 6a2 and 6a4 did not share this property with 6a1, a reason why 6a1 was chosen for many later studies.
Figure 6A:
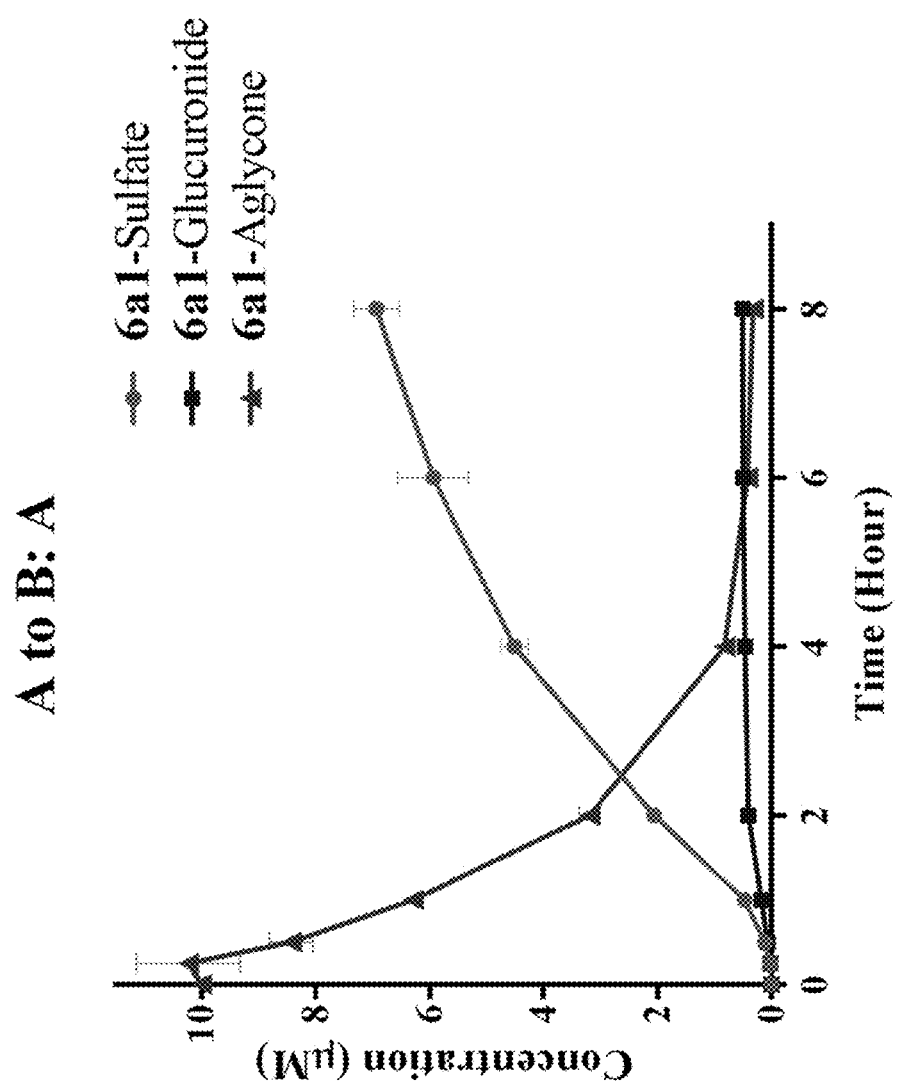
FIG. 6A is a graphical illustration of metabolism and transport of 6a1 in the Caco-2 cell monolayer model. 10 µM 6a1 (solid triangles) was applied to the apical side of the Caco-2 cell monolayer model, and the concentrations of 6a1 and its metabolites (glucuronides, squares; sulfates, circles) were determined from 0-8 hours. This figure shows the concentrations of various species at the apical side (A to B: A).
Figure 6B:
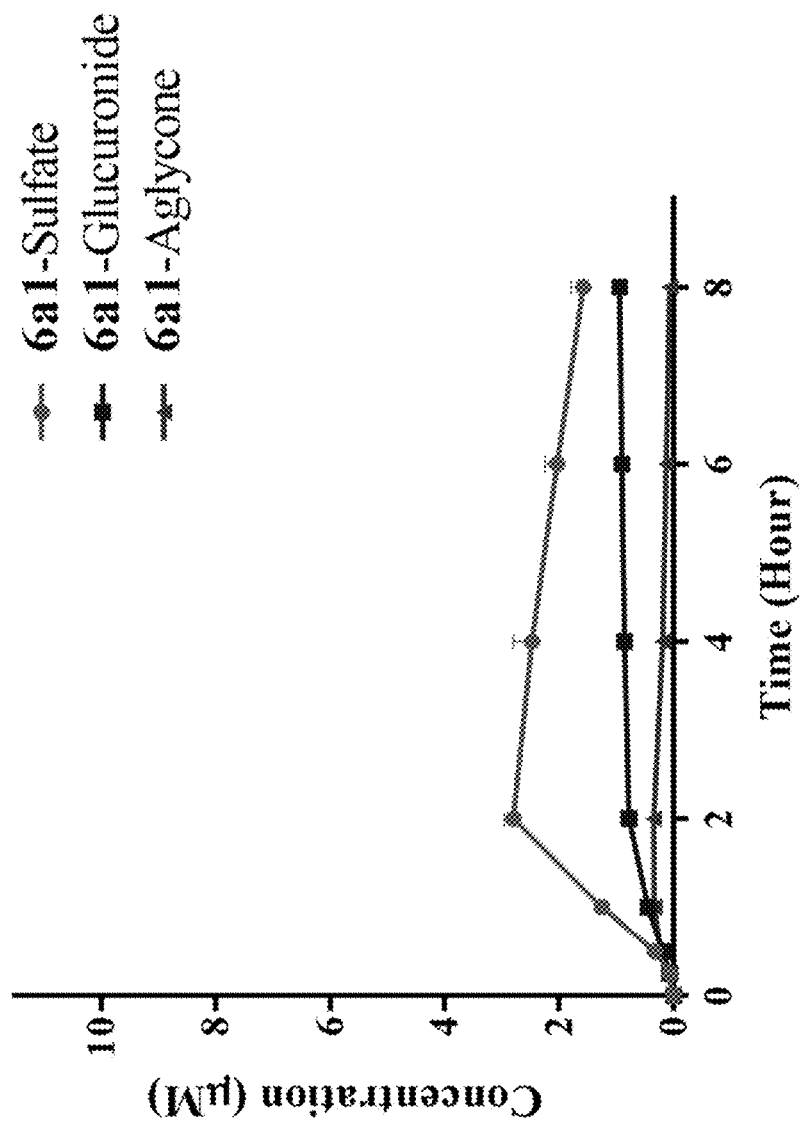
FIG. 6B is a graphical illustration of metabolism and transport of 6a1 in the Caco-2 cell monolayer model. 10 µM 6a1 (solid triangles) was applied to the apical side of the Caco-2 cell monolayer model, and the concentrations of 6a1 and its metabolites (glucuronides, squares; sulfates, circles) were determined from 0-8 hours. This figure shows the concentrations of various species at the basolateral side (A to B: B).
Figure 6C:
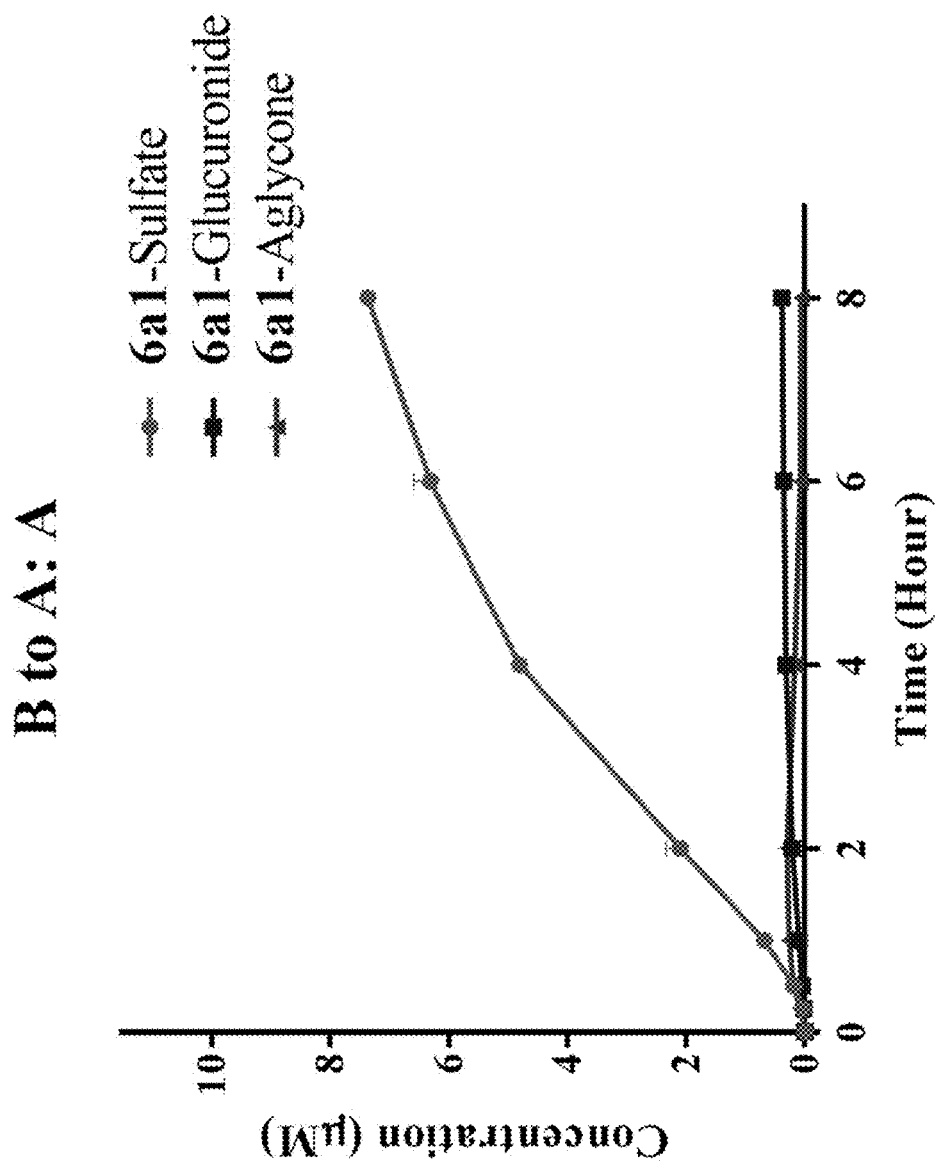
FIG. 6C is a graphical illustration of metabolism and transport of 6a1 in the Caco-2 cell monolayer model. 10 µM 6a1 was applied to the basolateral side of the Caco-2 cell monolayer model, and the concentrations of 6a1 and its metabolites (glucuronides, squares; sulfates, circles) were determined from 0-8 hours. This figure shows the concentrations of various species at the apical side (B to A: A).
Figure 6D:
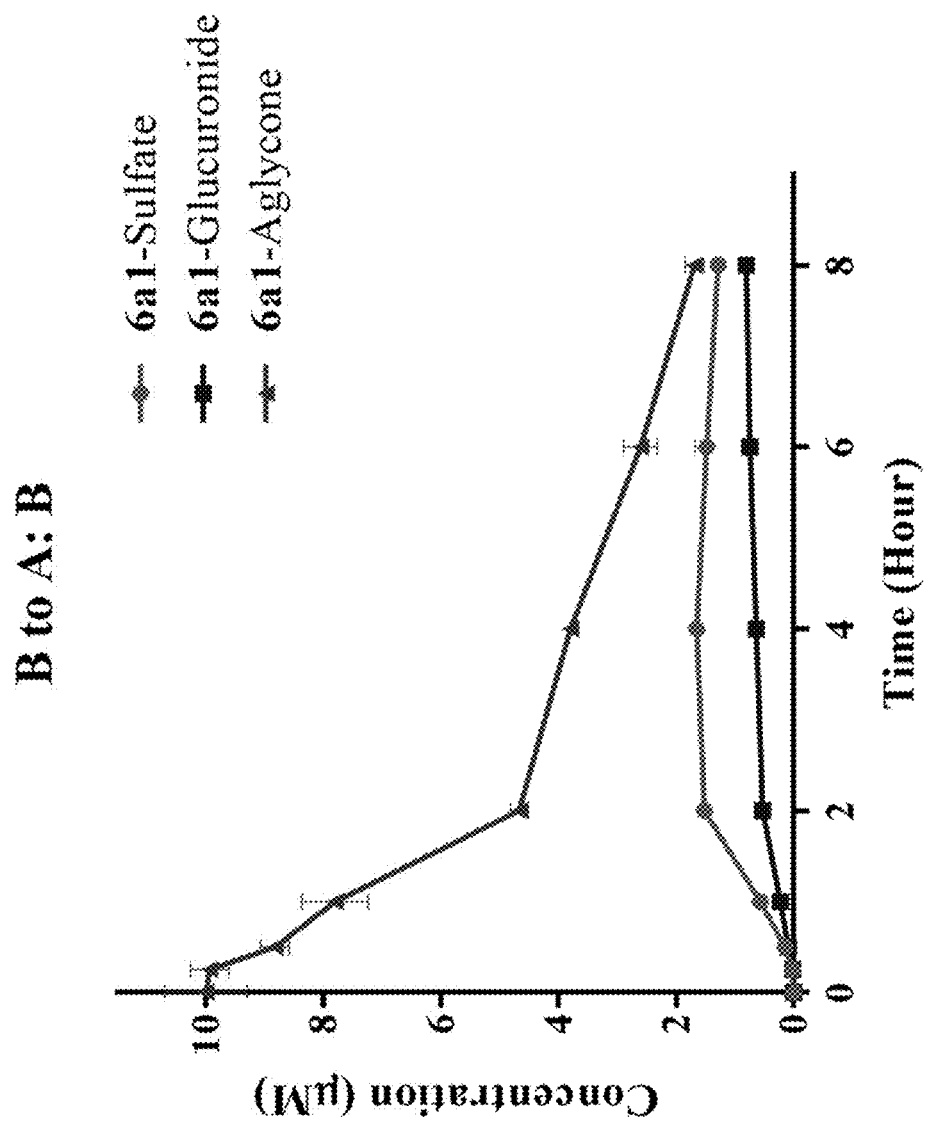
FIG. 6D is a graphical illustration of metabolism and transport of 6a1 in the Caco-2 cell monolayer model. 10 µM 6a1 was applied to the basolateral side of the Caco-2 cell monolayer model, and the concentrations of 6a1 and its metabolites (glucuronides, squares; sulfates, circles) were determined from 0-8 hours. This figure shows the concentrations of various species at the basolateral side (B to A: B).

For these phenolics, their metabolism rates were dependent on the R2 species, that is, the position of hydroxyl group on the aromatic ring. R1 species will not significantly influence the metabolism rates of these phenolic compounds. In experimentation, the glucuronidation rates of the phenolics with the same R2 (6a2, 6b2 and 6c2, or 6a3, 6b3 and 6c3) by rat liver microsomes were similar to each other (FIG. 5A). For both glucuronidation and sulfation, microsomes or S9 fractions prepared from rat liver were usually more efficient in conjugating the phenolics than those prepared from rat colon (FIG. 5B and FIG. 5C). Glucuronidation rates of 6a1-6a4 by human liver and intestinal microsomes are shown in FIG. 5D. For glucuronidation, microsomes prepared from human liver were usually more efficient in conjugating the phenolics than those prepared from human intestines. In general, among the phenolics, 6a1 and 6a2 were usually metabolized more rapidly than the other two compounds in rats, and liver conjugating activities were higher than the colonic activities.

Additional in vitro metabolism rates of newly synthesized COX-2 selective inhibitors by rat and human liver, intestine, or colon microsomes and S9 fractions are listed in Tables 3 and 4. These results suggest that these compounds are likely to be metabolized similarly in humans and rats, and therefore, they are likely to be only active in colon epithelium and not systemically.

TABLE 3

Glucuronidation and sulfation rates by rat intestinal and liver microsomes or S9 fractions

| Compound | Glucuronidation rates by liver microsomes (pmole/mg/min) | | Sulfation rates by liver S9 (pmole/mg/min) | | Glucuronidation rates by colon microsomes (pmole/mg/min) | | Sulfation rates by colon S9 (pmole/mg/min) | |
|---|---|---|---|---|---|---|---|---|
| | Mean | SD | Mean | SD | Mean | SD | Mean | SD |
| 6a1 | 6299 | 400 | 393 | 44 | 1111 | 18 | 49 | 9 |
| 6b1 | 7453 | 843 | 444 | 71 | ND | ND | ND | ND |
| 6c1 | 7026 | 232 | 534 | 56 | ND | ND | ND | ND |
| 6a2 | 3570 | 100 | 1096 | 34 | 1199 | 10 | 84 | 27 |
| 6b2 | 4132 | 50 | 876 | 126 | ND | ND | ND | ND |
| 6c2 | 3092 | 84 | 922 | 56 | ND | ND | ND | ND |
| 6a3 | 590 | 11 | 69 | 11 | 301 | 7 | 4 | 1 |
| 6b3 | 656 | 49 | 56 | 9 | ND | ND | ND | ND |
| 6c3 | 934 | 49 | 81 | 13 | ND | ND | ND | ND |
| 6a4 | 4763 | 620 | 32 | 8 | 571 | 16 | 4 | 3 |
| 7a1 | 1050 | 10 | 1150 | 170 | 160 | 10 | 40 | 0 |
| Raloxifene | 402 | 18 | 100 | 2 | 54 | 4 | 0 | 0 |
| Genistein | 2199 | 145 | 77 | 3 | 142 | 137 | 4 | 1 |

TABLE 4

Glucuronidation and sulfation rates by human intestinal and liver microsomes or S9 fractions

| Compound | Glucuronidation rates by liver microsomes (pmole/mg/min) | | Sulfation rates by liver S9 (pmole/mg/min) | | Glucuronidation rates by intestine microsomes (pmole/mg/min) | | Sulfation rates by human intestine S9 (pmole/mg/min) | | Glucuronidation rates by human Colon S9 (pmole/mg/min) | | Sulfation rates by human Colon S9 (pmole/mg/min) | |
|---|---|---|---|---|---|---|---|---|---|---|---|---|
| | Mean | SD | Mean | SD | Mean | SD | Mean | SD | Mean | SD | Mean | SD |
| 6a1 | 11576 | 77 | 55 | 2 | 2786 | 180 | 977 | 17 | 1080 | 220 | 110 | 0 |
| 6a2 | 1512 | 24 | 72 | 17 | 924 | 9 | 1141 | 22 | ND | ND | ND | ND |
| 6a3 | 60 | 4 | 7 | 1 | 45 | 5 | 29 | 0 | ND | ND | ND | ND |
| 6a4 | 291 | 14 | 57 | 10 | 2134 | 30 | 750 | 30 | ND | ND | ND | ND |
| 7a1 | 2510 | 10 | 40 | 0 | ND | ND | ND | ND | 190 | 10 | 40 | 0 |
| Raloxifene | 681 | 25 | 19 | 2 | 2846 | 29 | 58 | 1 | ND | ND | ND | ND |
| Genistein | 965 | 21 | 24 | 2 | 4665 | 47 | 46 | 1 | ND | ND | ND | ND |

Compound 6a1 was the first compound synthesized and demonstrated to be effective in situ. It is likely that other compounds, such as 7a1, will be shown to be more active than 6a1, but the principle demonstrated using 6a1 is applicable to all relevant compounds.

Example 5

Metabolism and Transport of 6a1 Across the Caco-2 Cell Monolayers

The Caco-2 cell monolayer is a well-established FDA-recognized model to study the absorption, transport, and metabolism of drugs in the human gastrointestinal tract. This allows for prediction of the disposition of the new compounds in colonic epithelium that is also undergoing carcinogenesis, because Caco-2 is a human colorectal cancer cell line.

After 10 µM 6a1 was applied to the apical or basolateral side of the Caco-2 monolayer model, the concentrations of 6a1 and its main phase II metabolites, glucuronide and sulfate, were monitored at both sides (FIG. 6A-D). The concentration of aglycone was also monitored at both sides. The results showed that 6a1 permeated the Caco-2 cell membrane easily and was rapidly conjugated by UGTs and SULTs inside the cells. The dominant metabolites were found to be sulfates. The majority of sulfates were effluxed to the apical side, while less was transported to the basolateral side. The amount of glucuronide generated by Caco-2 cells was much less than that of sulfates. The glucuronide was also transported to both sides.

The rapid phase II metabolism and active apical efflux of the metabolites in the intestinal epithelium have been observed in the intestinal disposition of a number of phenolic phytochemicals, especially flavonoids. The metabolites effluxed to the intestinal lumen can be hydrolyzed by colonic bacteria, and the resulting aglycones are available for absorption again (FIG. 2A). This process named "enteric recycling" can slow down the decrease of drug concentrations in the intestinal lumen, and make more unconjugated drug molecules available inside the colonic epithelial cells.

Example 6

Pharmacokinetics of Celecoxib, 6a1 and 6a3 in Rats

The aim of designing locally bioavailable COX-2 inhibitors is to diminish the risk of cardiovascular events by lowering their exposure to the cardiovascular system. Thus, after in vitro characterization of their metabolism, the pharmacokinetics of 6a1 and 6a3 were investigated in Sprague-Dawley (SD) rats after oral administration and the results were compared with that of celecoxib. The drugs were dispersed in ORA-PLUS® suspension vehicle (from Paddock Laboratories, Minneapolis, Minn.) and administrated to SD rats by oral gavage. The blood samples were collected from the tail tips at different time points.

Figure 7A:
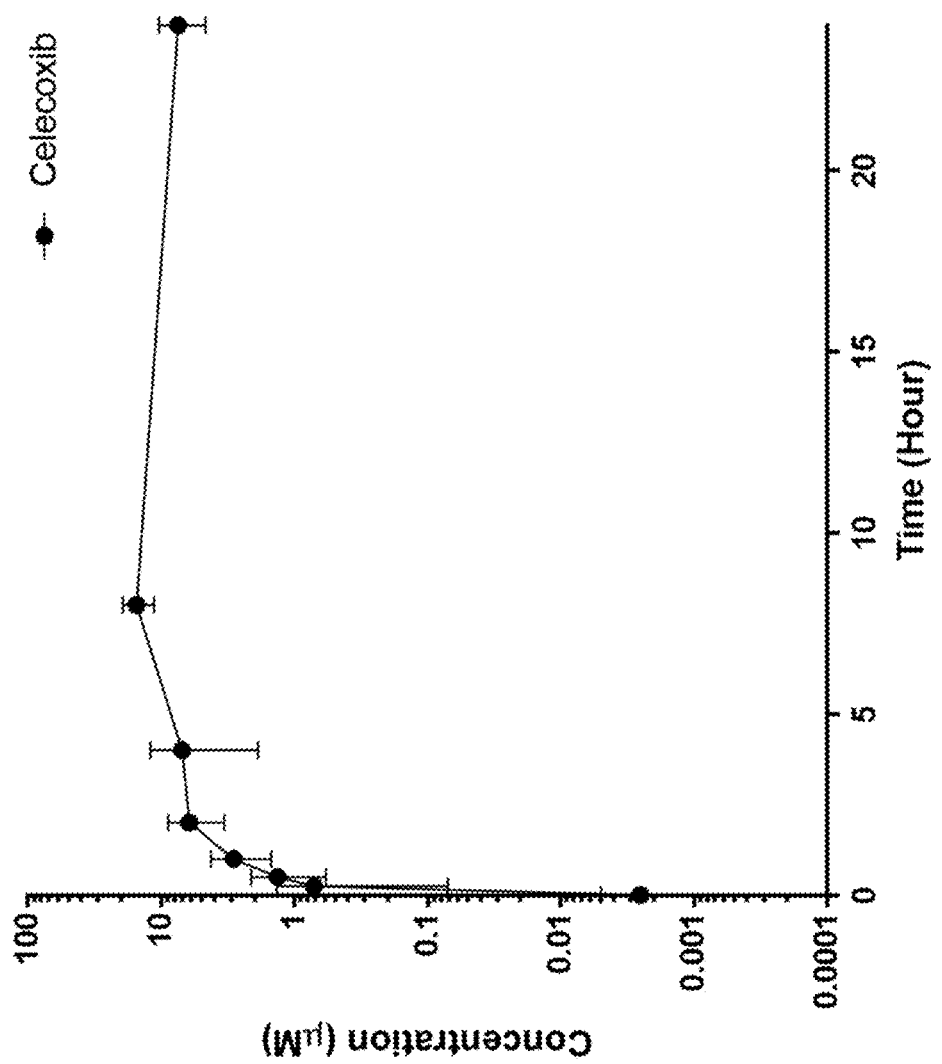
FIG. 7A is a graphical illustration of the blood concentrations of celecoxib in pharmacokinetics studies (n=5-6 in each experiment). The blood concentrations of celecoxib after an oral dose of 20 mg/kg in SD rats.

After an oral dose of 20 mg/kg celecoxib in SD rats, the drug was rapidly absorbed and the blood concentration exceeded 1 µM in 30 minutes. The peak blood concentration, reached 8 hours after oral administration, was as high as 15.40±4.01 µM, which was 5000 fold of its IC50 value against COX-2 (FIG. 7A). In healthy human adults, the peak concentration of celecoxib in the plasma was higher than 2 µM after a single oral dose of 200 mg celecoxib [15]. The high blood concentration and low IC50 value ensured the therapeutic effects of celecoxib in patients with arthritis, but also result in the increased risk of cardiovascular events.

Figure 7B:
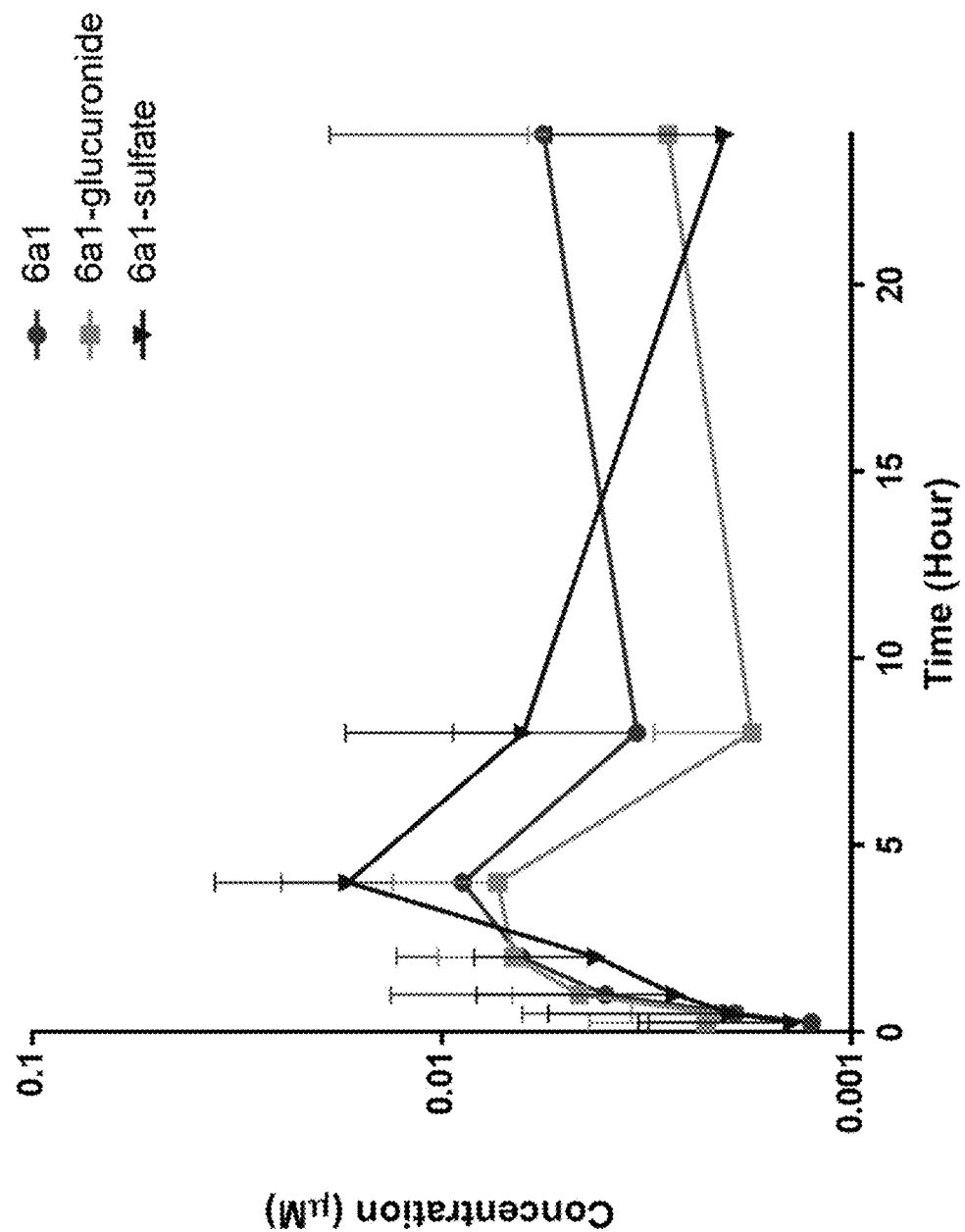
FIG. 7B is a graphical illustration of the blood concentrations of the locally bioavailable COX-2 inhibitors in pharmacokinetics studies (n=5-6 in each experiment). The blood concentrations of 6a1 and its two phase II metabolites after an oral dose of 20 mg/kg in SD rats. Please note that the concentration of 6a1 is about 1000 fold less than celecoxib shown in FIG. 7A.
Figure 7C:
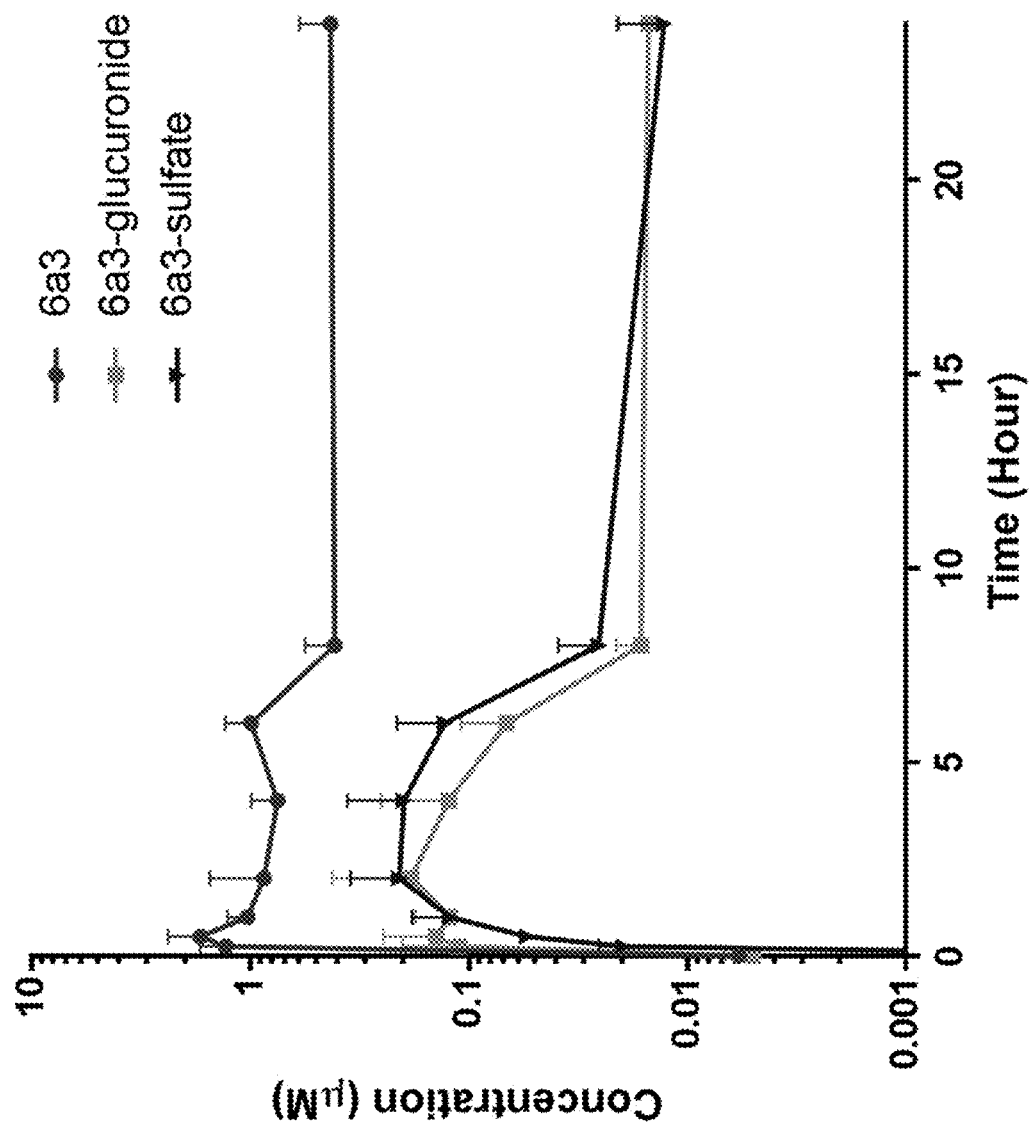
FIG. 7C is a graphical illustration of the blood concentrations of the locally bioavailable COX-2 inhibitors in pharmacokinetics studies (n=5-6 in each experiment). The blood concentrations of 6a3 and its two phase II metabolites after an oral dose of 20 mg/kg in SD rats. Please note that the concentration of 6a1 is about 100 fold less than celecoxib shown in FIG. 7A.

After an oral dose of 20 mg/kg 6a1 in SD rats, however, only trace concentrations of 6a1 and its metabolites could be detected in the blood during the pharmacokinetics studies (FIG. 7B). In the 24 hours after the administration, the blood concentrations of 6a1 and its metabolites never exceeded 0.02 µM, indicating that only a marginal amount of 6a1 entered the systemic circulation of rats. The extensive first-pass metabolism could be responsible for the low oral bioavailability of 6a1, although a limited absorption of 6a1 in the intestinal tract can also be the reason. The pharmacokinetic study of 6a3 was conducted and compared to the result with that of 6a1. 6a3 shares the same molecular weight and very similar structure and physicochemical properties with 6a1 (Table 1), but in the in vitro characterizations 6a3 has been demonstrated as a relatively poor substrate of phase II metabolism enzymes from humans and rats (FIG. 5A-5D). After an oral dose of 20 mg/kg 6a3 in SD rats, the peak blood concentration of 6a3 was 1.69 µM, and the blood levels of the two phase II metabolites of 6a3 were much lower than that of the parent (FIG. 7C). With the similar structures and LogP values, 6a3 possesses a much better oral bioavailability than 6a1, implying that the different first-pass metabolism rates accounted for the difference in pharmacokinetic properties between the two. Later in this disclosure, in the perfused rat colon model, the first-pass metabolism and excretion of 6a1 in rat liver are disclosed with more details.

Figure 7D:
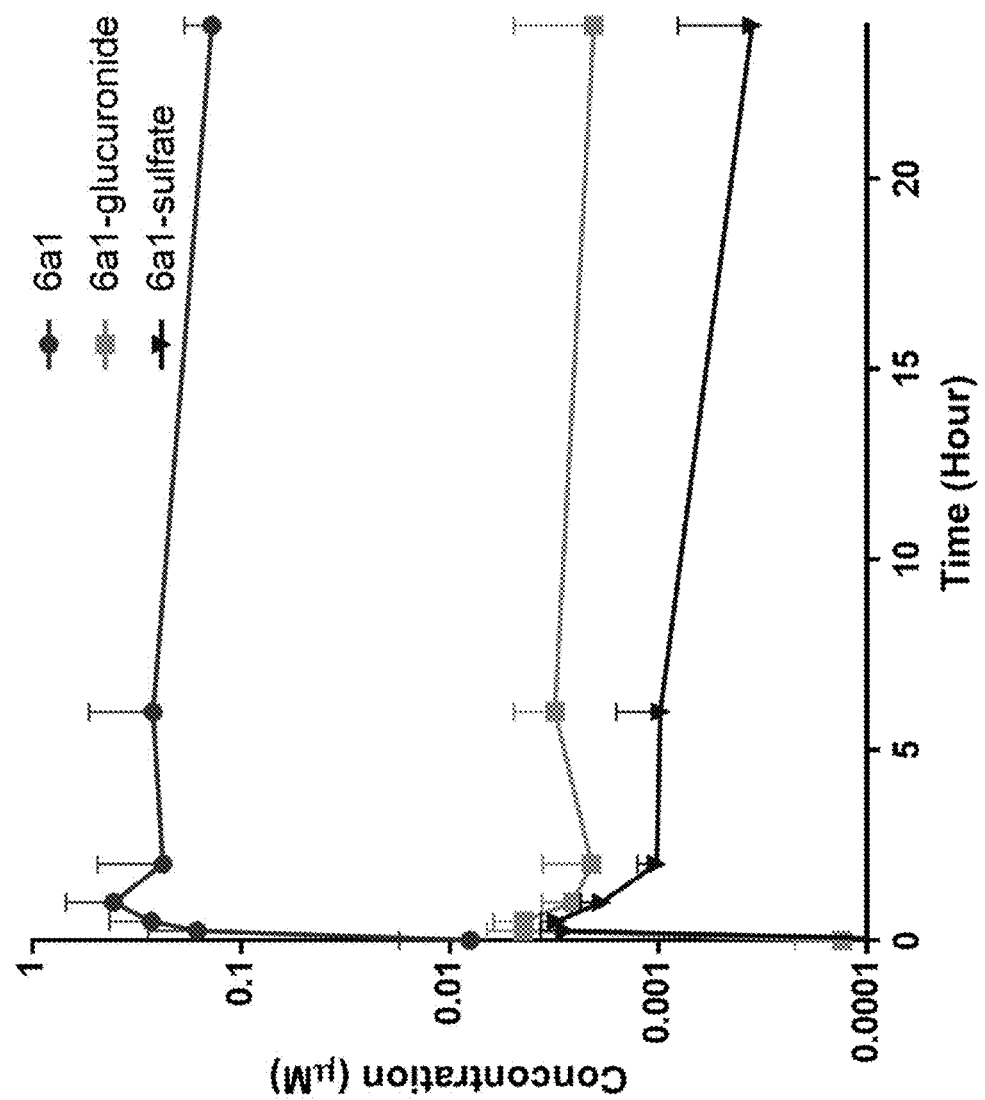
FIG. 7D is a graphical illustration of the blood concentrations of the locally bioavailable COX-2 inhibitors in pharmacokinetics studies (n=5-6 in each experiment). The blood concentrations of 6a1 and its two phase II metabolites after a dose of 20 mg/kg administrated to colon from the anus in SD rats. Please note that the concentration of 6a1 is about 300 fold less than celecoxib shown in FIG. 7A.

The locally bioavailable COX-2 inhibitors are designed mainly for the treatment and chemoprevention of colonic diseases. Thus, in certain applications, the locally bioavailable COX-2 inhibitors could be delivered to the colon of animals or patients, avoiding the dissolution and absorption in the upper gastrointestinal tract and small intestine. Therefore, 20 mg/kg 6a1 was administered in suspension vehicle to the proximal colon of SD rats via a catheter reaching approximately 8 cm deep into the anus. Compared with the results after the oral administration, 6a1 was detected in the blood with higher concentrations after the intracolonic administration, but meanwhile its phase II metabolites were much lower than the parent (FIG. 7D). The 6a1 blood concentrations can be explained as that some 6a1 was absorbed from the rectum after the intracolonic administration and entered the systemic circulation via the middle and lower rectal veins, which helped 6a1 escape the first-pass metabolism in liver. For the same reason, lower levels of phase II metabolites were detected in the blood. In general, all the pharmacokinetic studies illustrated that the first-pass metabolism can efficiently diminish or even eliminate the systemic bioavailability of certain compounds. Thus, other delivery routes other than rectal suppositories can provide better results for the designed compounds.

Example 7

Efficacy of the Locally Bioavailable COX-2 Inhibitors in TNBS-Treated Rat Colon

Figure 8A:
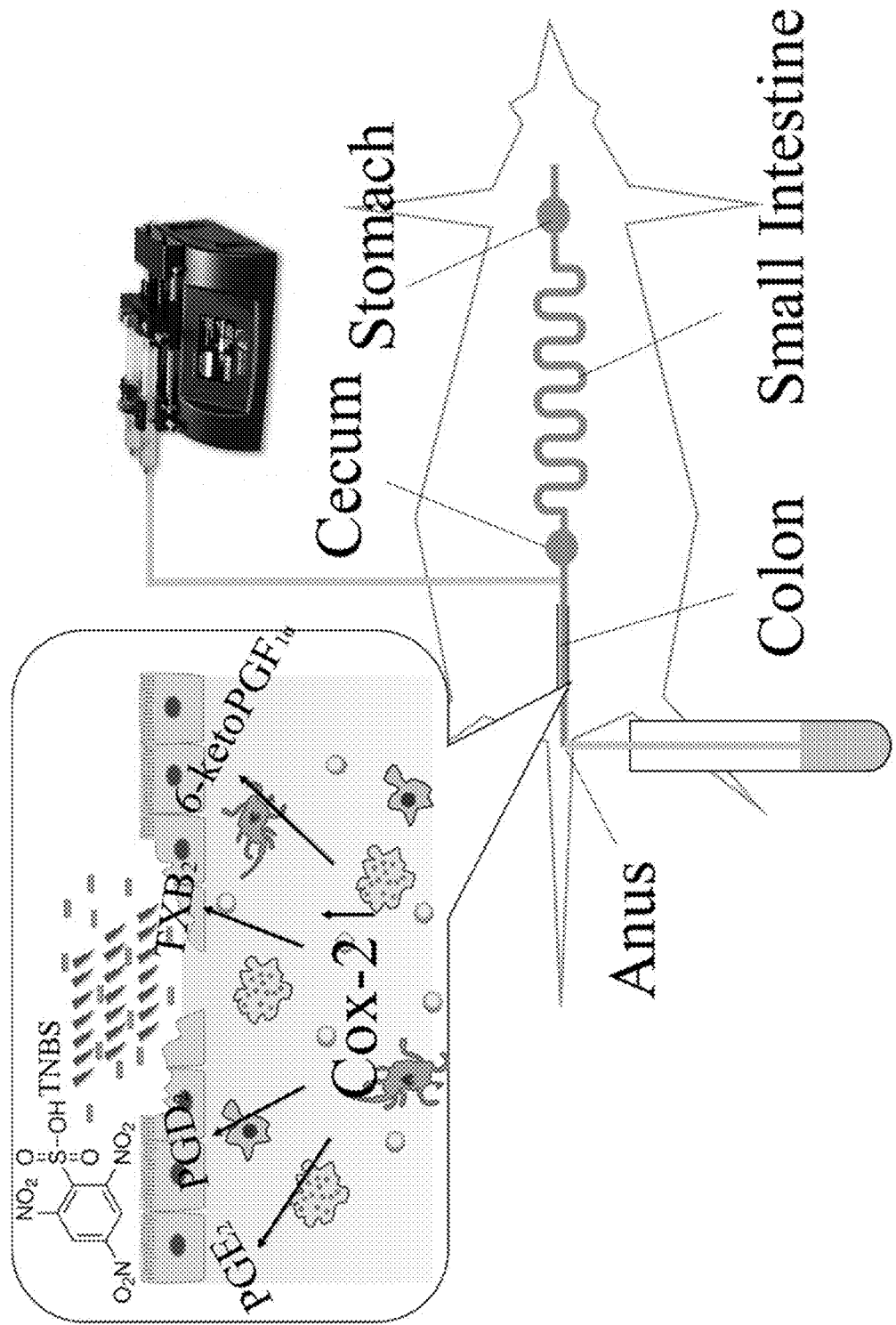
FIG. 8A is an illustration of a diagrammatic sketch of the colon perfusion system, which utilizes TNBS to create acute colitis.

The locally bioavailable COX-2 inhibitors were assessed for their inhibitory effects on COX-2 in rat colon. COX-2 is not expressed in healthy rat colon so a 2, 4, 6-trinitrobenzenesulfonic acid (TNBS)-induced acute colitis model was established. The experimental colitis in rat colon induced by TNBS is commonly used in inflammatory bowel disease (IBD) research and shares many histopathological and clinical features with human IBD. For example, the overexpression of inflammatory enzymes such as COX-2, 5-lipoxygenase (5-LOX) and inducible nitric oxide synthase (iNOs) are observed. Meanwhile, nitric oxide (NO), leukotrienes, prostaglandins and pro-inflammatory cytokines are released in the inflamed colon [16]. A substantial and stable expression of COX-2 protein could be detected in the inflamed rat colon between 12 to 24 hours after TNBS treatment [17]. Briefly, 30 mg TNBS in 200 µL 50% ethanol was administrated to the colon of SD rats via a catheter reaching approximately 8 cm proximal to the anus. 12 hours later, the rats were anesthetized and the segments of proximal colon were cannulated and flashed with saline to clean the fecal matter remaining. The cannulation tubes were connected to a perfusion pump and kept in a 37° C. water bath. (FIG. 8A). After perfusion with 0.5 mL/min blank Hank's Balanced Salt Solution (HBSS) in the initial hour to remove residual prostaglandins, the colon was perfused with HBSS containing vector (DMSO) or different concentrations of drugs for another 3 hours at the same flow rate. The perfusate was collected from the anus every 20 minutes (approximately 10 mL per tube), 2.5 ng/mL $PGE_2$-$d_4$ was added as the internal standard and concentrated by solid-phase extraction (SPE) before quantitative analysis.

Figure 8B:
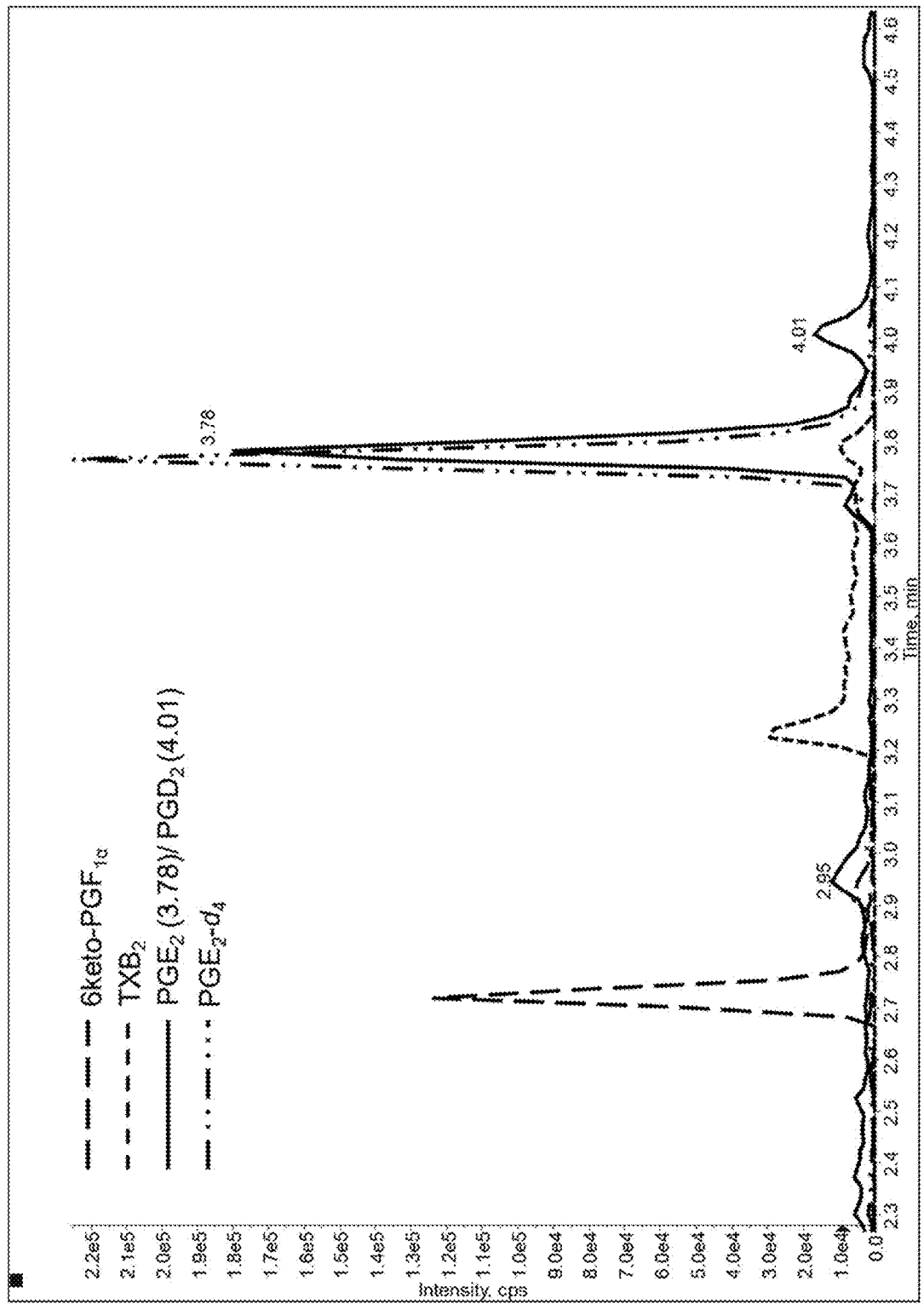
FIG. 8B is a representative mass spectrometry chromatograph for the analysis of prostaglandin concentrations in the perfusate.
Figure 9A:
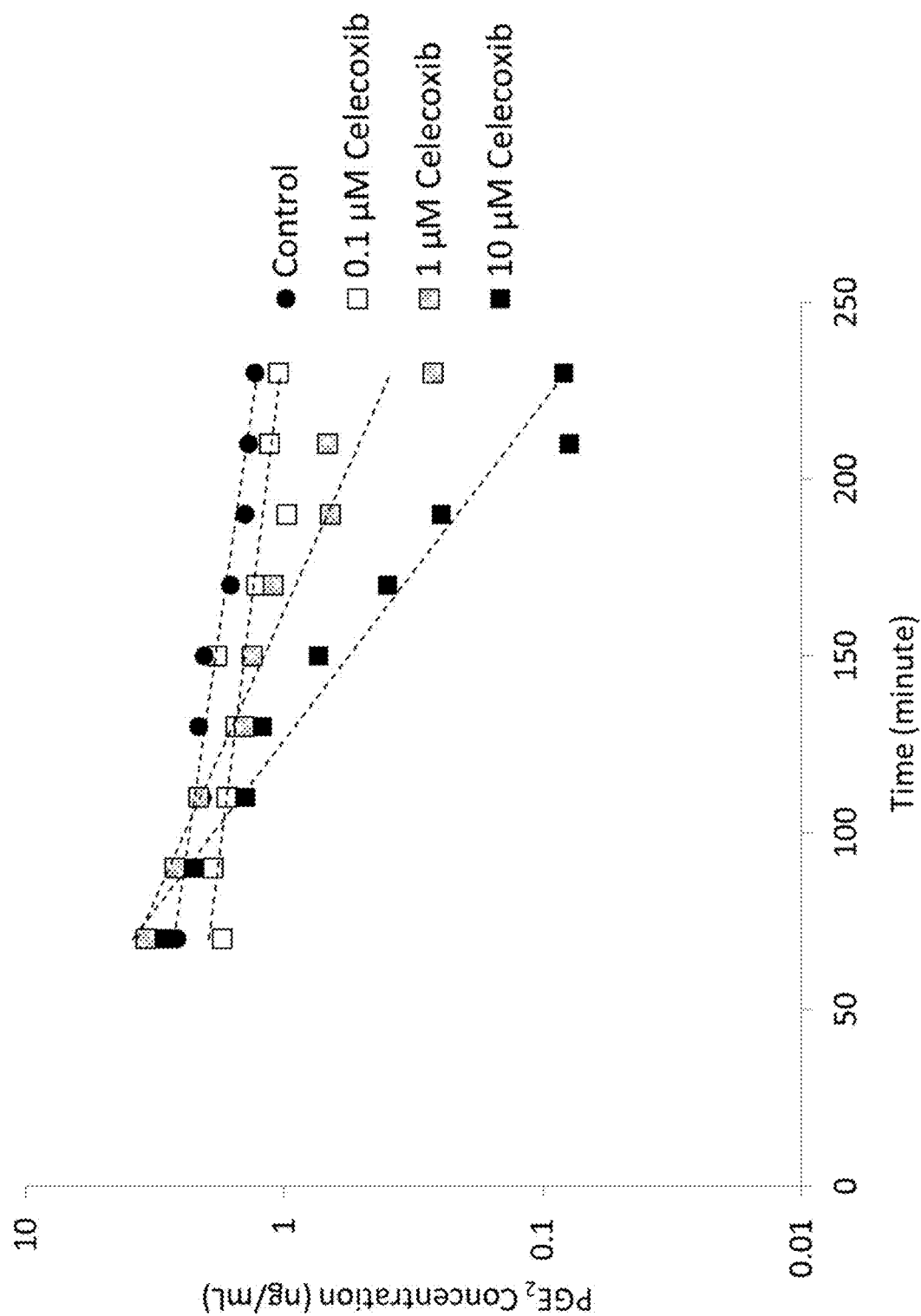
FIG. 9A is a graphical illustration of the attenuation of PGE2 concentrations in the perfusate from the inflamed rat colon. The decreasing of PGE2 concentrations in the perfusate can be described as a first order process and the rate constants were obtained by fitting the experimental results to the equation $C=C60\ \mathrm{minxe}^{-kt}$. 1 and 10 µM celecoxib significantly accelerated the PGE2 attenuation in the perfusate, while 0.1 µM was found to be ineffective.
Figure 9B:
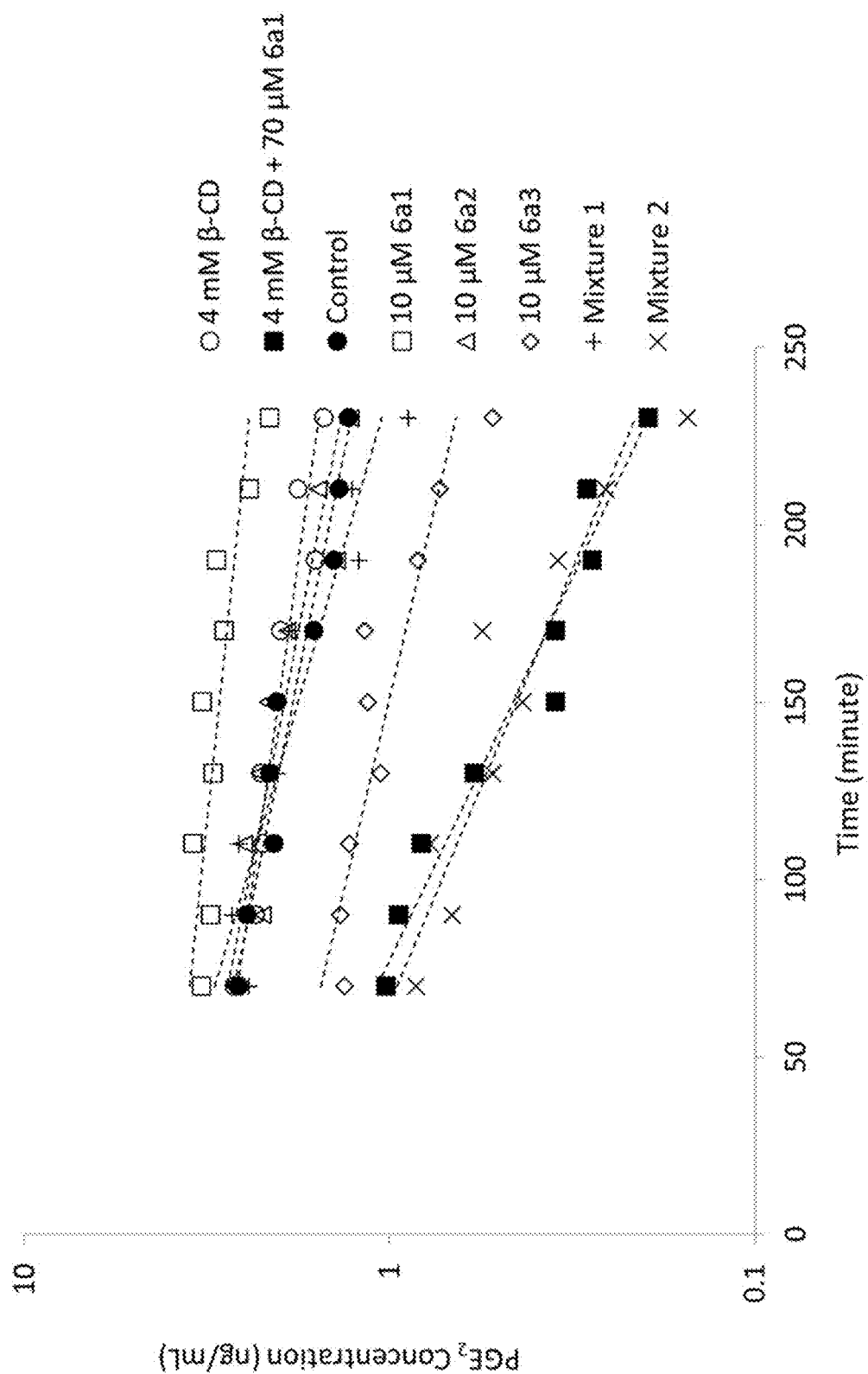
FIG. 9B is a graphical illustration of the attenuation of PGE2 concentrations in the perfusate from the inflamed rat colon. The influences of the locally bioavailable COX-2 inhibitors on the PGE2 attenuation. Perfusion with β-CD-formulated 70 µM 6a1 or mixture 2 (6a1-3, 6b2-3, and 6c2-3, 10 µM for each) significantly accelerated the PGE2 attenuation, while all the other attempts failed to show effectiveness.

In UPLC-MS/MS analysis of the concentrated perfusate from TNBS-treated colon, four prostaglandins can be detected as the major product from COX-2 pathway. (FIG. 8B) Among the four prostaglandins, PGE2 was selected as the indicator of COX-2 activity because it was the most abundant signal in this model. In the control group perfused with HBSS containing DMSO, the concentrations of PGE2 in the perfusate were decreasing during the perfusion period and its attenuation upon time could be appropriately described as a first-order process. The rate constants and half-lives of PGE2 concentration attenuation were obtained by fitting an exponential equation to the results (FIG. 9A and FIG. 9B). In the control group, the average half-life of PGE2 attenuation was 156±49 min, while in the groups perfused with 0.1, 1 and 10 µM celecoxib the half-life was 127±36, 70±19, and 37±4 min, respectively. 1 and 10 µM celecoxib significantly decreased the half-life of PGE2 concentration attenuation, showing the inhibitory effect of celecoxib on colonic COX-2 activity (FIG. 9C). 0.1 µM celecoxib was not effective, illustrating that the inhibitory effect was dependent on the celecoxib concentration used for the experiment.

Figure 9C:
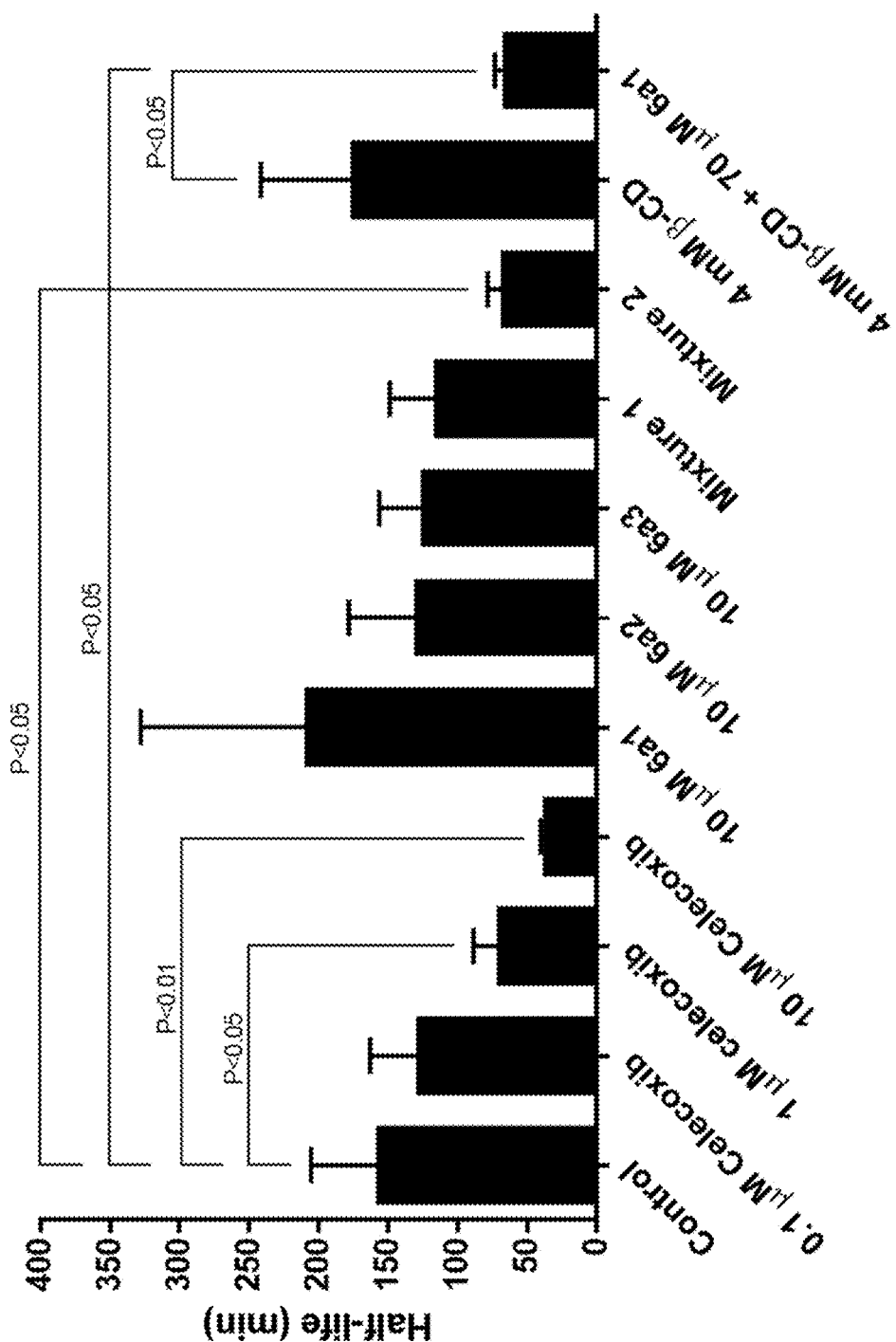
FIG. 9C is a graphical illustration of the attenuation of PGE2 concentrations in the perfusate from the inflamed rat colon. The comparison of the half-lives of PGE2 attenuation in each group. The half-lives were derived from the rate constants and the P values are shown in the figure for the statistical analysis (T-test).

In the groups perfused with the locally bioavailable COX-2 inhibitors, perfusion with 10 µM 6a1, 6a2 or 6a3 respectively did not significantly alter the half-lives of $PGE_2$ concentration attenuation. When 6a1, 6a2, 6b2 and 6c2 were combined in the perfusate (FIG. 9C, mixture 1, 10 µM for each), there was mild but not statistically significant inhibitory effects on $PGE_2$ production (P=0.17 with the control group). However, when a more comprehensive mixture of 6a1, 6a2, 6a3, 6b2, 6b3, 6c2 and 6c3 was assessed for its efficacy (FIG. 9C, mixture 2, 10 µM for each), the inhibitory effect was found to be similar to that of 1 µM celecoxib. Considering that the locally bioavailable COX-2 inhibitors were approximately 50 fold less potent than celecoxib (Table 1), their concentrations in the perfusate were related to their efficacy to inhibit colonic COX-2 in the TNBS-treated rat colon model. However, due to the hydrophobic properties of the locally bioavailable COX-2 inhibitors, a concentration higher than 10 µM in HBSS could hardly be achieved by simply increasing the amount of solute in the solution. Thus, β-cyclodextrin ((β-CD), an excipient which was often used in pharmaceutical development was employed to increase the apparent solubility of the locally bioavailable COX-2 inhibitors in HBSS [18, 19]. After sonication and subsequent centrifuge to remove undissolved substances, the solubility of 6a1 in HBSS was increased to as high as 70 µM in the presence of 4 mM β-CD. The osmotic pressure of the solution was determined as 290 mOsm/kg and physiologically appropriate for in situ perfusion studies in rat colon. Perfusion with β-CD-formulated 70 µM 6a1 in the inflamed rat colon successfully and significantly decreased the half-life of PGE2 attenuation to 66 min, which was comparable to that of 1 µM celecoxib, while the perfusion with 4 mM β-CD alone did not have any effects on $PGE_2$ production in the inflamed rat colon (FIG. 9C). The efficacy differences between celecoxib and 6a1 shown in the inflamed rat colon model can be correlated with their $IC_{50}$S on COX-2 activity determined in the in vitro models (Table 1).

Example 8

The Metabolism and Excretion of 6a1 in Rats During TNBS Treated Colon Perfusion

The perfusion of celecoxib and locally bioavailable COX-2 inhibitors in the TNBS-treated rat colon also helped investigate their absorption, metabolism and excretion properties. For this purpose, blood samples were collected from each rat every hour during the perfusion period, and the bile samples were also collected by cannulating the bile duct.

Figure 10A:
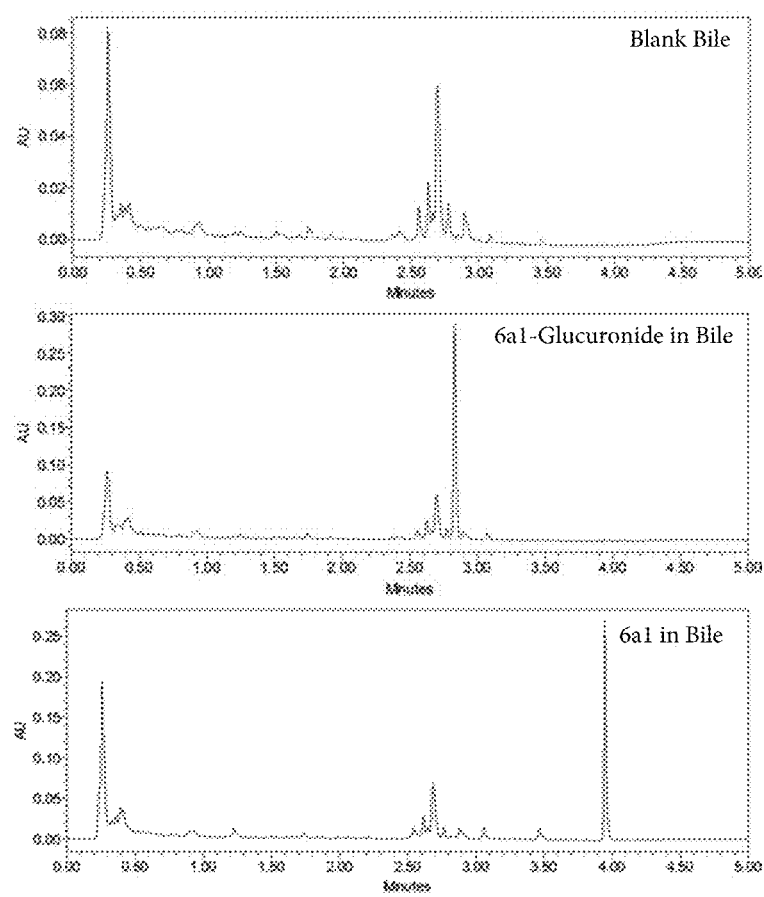
FIG. 10A is an illustration of the absorption, metabolism and excretion of 6a1 in the rat colon and liver.
Figure 10B:
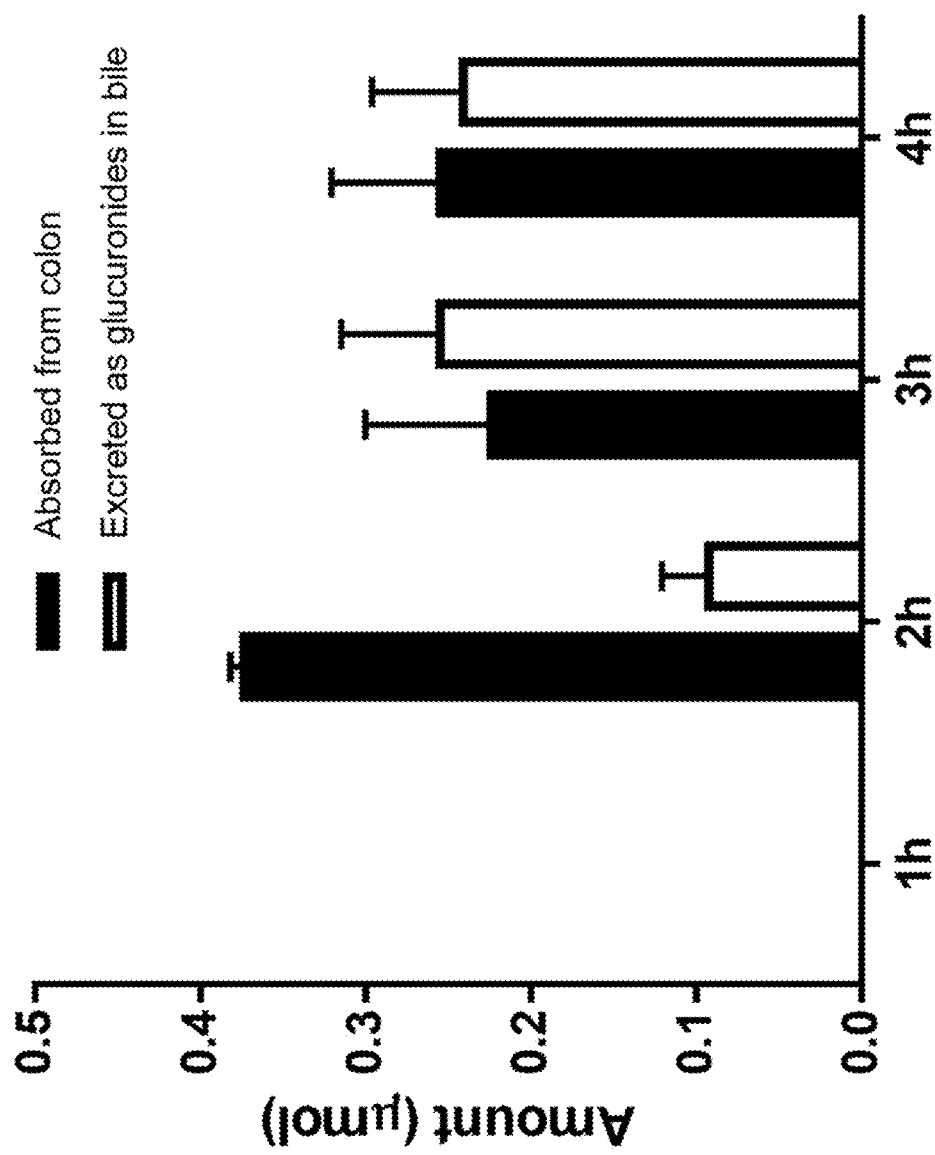
FIG. 10B is an illustration of the absorption, metabolism and excretion of 6a1 in the rat colon and liver.

The lead compound 6a1 was designed and validated as an excellent substrate in phase II drug metabolism pathways in vitro, especially glucuronidation by the liver (FIG. 5A-5D). The analysis of bile and peripheral blood samples would demonstrate that it is possible to take advantage of the extensive first-pass metabolism of 6a1 in the liver to largely minimize the drug concentrations in the systemic circulation in vivo. By comparing the 6a1 concentrations in the input and output perfusate containing β-CD-formulated 6a1, the amounts of 6a1 absorbed from the colon were calculated for each hour during the perfusion period (FIG. 10B). Approximately 13% of the total 6a1 perfused was absorbed in the colon, illustrating that β-CD-formulated 6a1 could rapidly penetrate the colonic epithelium. Meanwhile, only negligible amounts of 6a1 glucuronide and sulfate were excreted to the perfusate, which were both lower than 0.5% of the absorbed amount of 6a1. The rat colonic epithelium showed a limited ability in conjugating 6a1, demonstrated when studying the possible metabolism of other phenolic compounds such as genistein and apigenin in rat colon [20].

Unlike the rat colon, the rat liver was found to be extremely powerful in metabolizing 6a1, and the predominant pathway was glucuronidation. UPLC-UV analysis of the extracted bile samples collected during 6a1 perfusion showed that 6a1-glucuronide could reach more than 200 μM (FIG. 10A). The amounts of 6a1 metabolized in liver and excreted to bile in each hour were shown in FIG. 10B. From the beginning to the end of the perfusion period, approximately 75% (on average) of the absorbed 6a1 could be recovered from bile as glucuronides. In the 3rd and 4th hours of perfusion when the absorption of 6a1 in colon and the excretion of 6a1-glucuronides in bile reached the steady state, almost 100% of 6a1 absorbed was subject to biliary excretion in the liver (FIG. 10B).

Figure 11A:
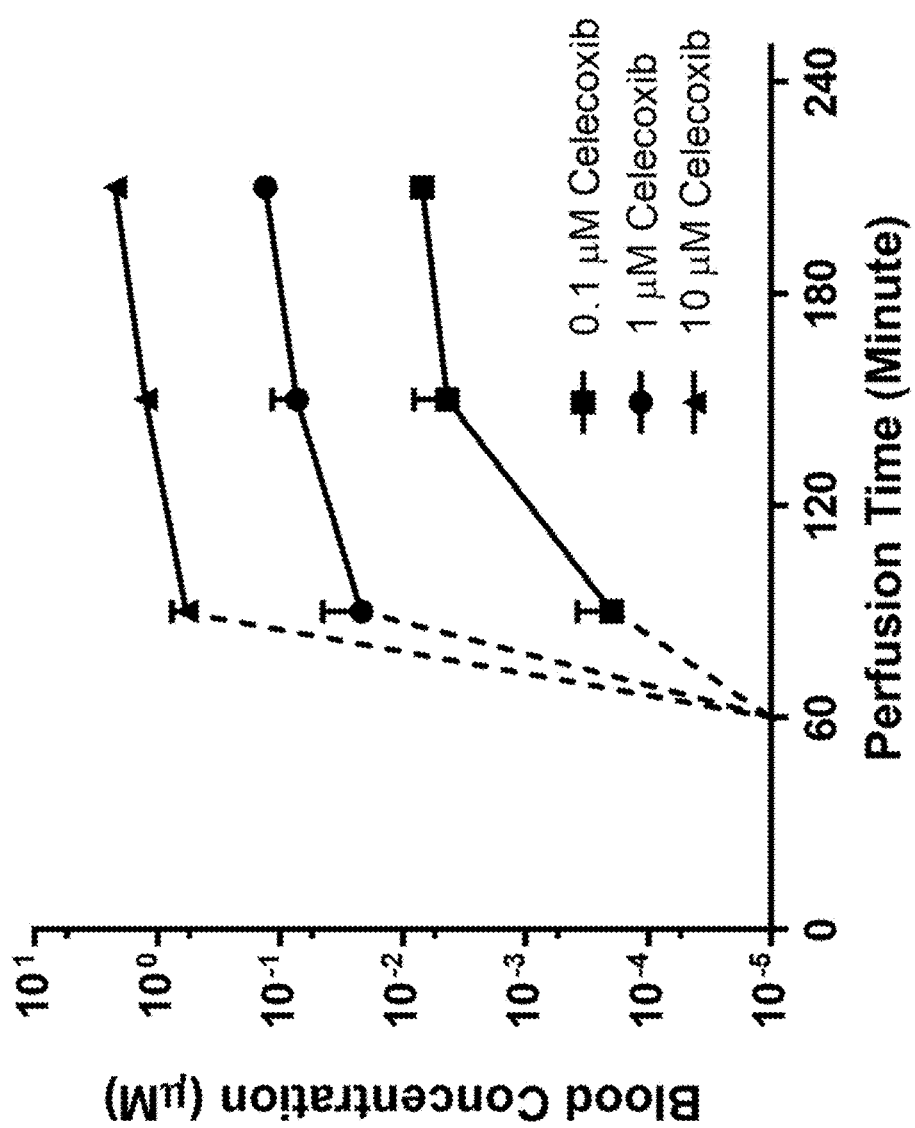
FIG. 11A is a graphical illustration of the concentrations of celecoxib in the blood samples collected from the rat tails during the perfusion periods.

The major metabolism pathways for the elimination of celecoxib in rats and humans are oxidation by hepatic phase I metabolism enzymes CYP450s [21]. The modest metabolism rate of celecoxib in the liver guarantees that its blood concentration can be above the therapeutic window for a reasonable term in the treatment of arthritis, but also results in the exposure of the cardiovascular system to high concentrations of celecoxib, leading to increased risk of cardiovascular events [22]. The analysis of the blood samples withdrawn from rat tail showed that celecoxib were accumulated in the systemic circulation during the perfusion of rat colon with 0.1, 1, and 10 μM celecoxib in HBSS (FIG. 11A). The blood concentrations of celecoxib were higher than 1 μM when the rat colon was perfused with 10 μM celecoxib. Considering that the $IC_{50}$ of celecoxib on COX-2 activity was as low as 0.003 μM (Table 1), the blood concentration (0.15 μM) was approximately 50 fold of the $IC_{50}$ value when the rat colon was perfused with 1 μM celecoxib which was the lowest concentration required to inhibit colonic COX-2 (FIG. 11A). Thus, a high risk of cardiovascular events can be expected when celecoxib is used as a routine agent in the treatment of colonic inflammatory diseases or CRC chemoprevention.

Figure 11B:
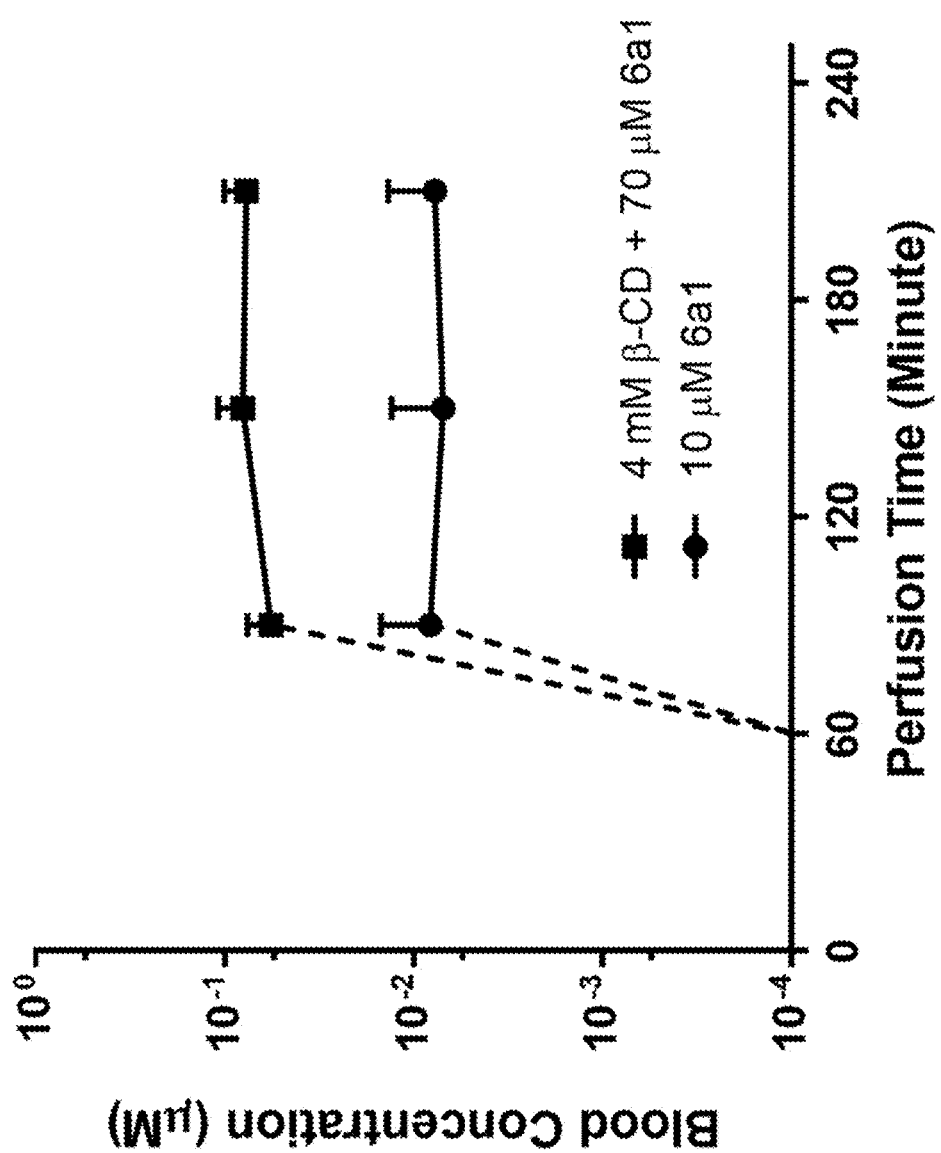
FIG. 11B is a graphical illustration of the concentrations of 6a1 in the blood samples collected from the rat tails during the perfusion periods.

The blood concentration of 6a1 in rat when the TNBS treated colon was perfused with 10 μM or 70 μM (β-CD-formulated) 6a1. With or without β-CD formulation in the perfusate, the 6a1 blood concentration achieved a plateau soon after the perfusion began, indicating an efficient first-pass elimination which prevented 6a1 from entering the systemic circulation (FIG. 11B). β-CD enhanced the solubility of 6a1 in HBSS, which also increased the blood concentration of 6a1. However, it should be noticed that the 6a1 blood concentration (0.08 μM) was still much lower than its $IC_{50}$ on COX-2 activity when the colonic COX-2 was inhibited by 70 μM 6a1 in the perfusate. In addition, no glucuronide and sulfate of 6a1 were detected in the peripheral blood samples, indicating an exclusive excretion of the phase II conjugates to bile in the liver. More importantly, the phase II conjugates excreted in bile can be hydrolyzed by and then reabsorbed in the colon, completing the enterohepatic circulation. In humans and animals, the enteric circulation of 6a1 is also possible after the phase II conjugates are excreted to the lumen from the colonic epithelium and then hydrolyzed by bacteria hydrolases (e.g., glucuronidases and sulfatase) (FIG. 6). Either the enterohepatic or enteric circulation can help maintain local drug concentrations and prolong their residence time in the colon, which are quite beneficial in the treatment of various colonic diseases.

Figure 12:
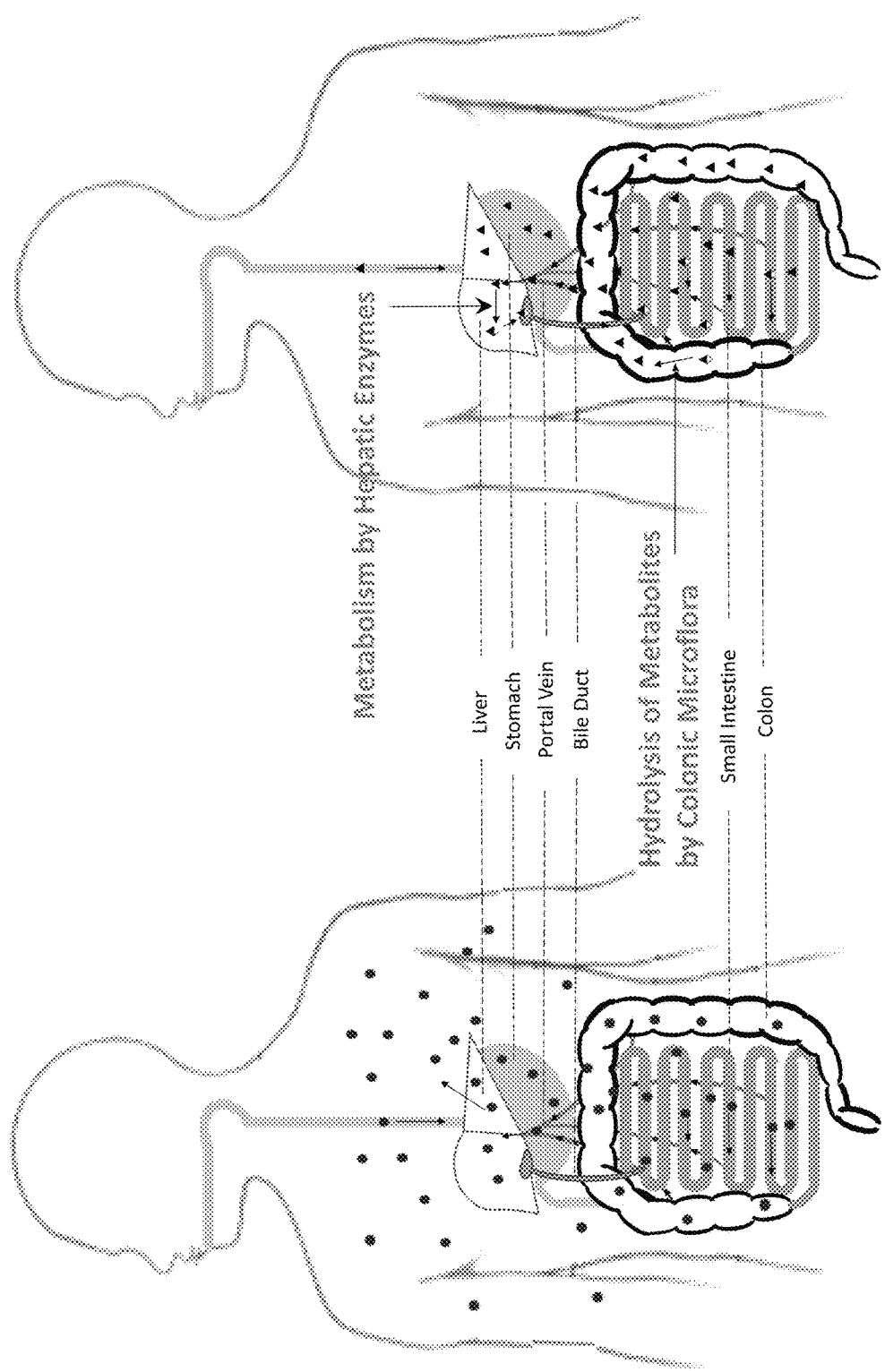
FIG. 12 is a depiction of the pharmacokinetic properties between systemically bioavailable COX-2 inhibitors and the locally bioavailable COX-2 inhibitors in the human body after administration. The distribution of the locally bioavailable COX-2 inhibitors and their metabolites are limited to the gut and liver due to the extensive first-pass metabolism and enterohepatic circulation. The high concentration of systemically bioavailable COX-2 inhibitors (e.g., celecoxib) in the systemic circulation increases the risk of cardiovascular events in patients.

In an embodiment, compounds can be built with phenolic hydroxyl groups that are highly susceptible to glucuronidation and or sulfonation in their structures. These compounds inhibit colonic COX-2 activity and are locally active when a high enough concentration is achieved in the colonic lumen and colon tissue after administration of drugs formulated to release the drugs in the colon. These compounds with phenolic groups can be inactivated by the first-pass metabolism. The COX-2 inhibitors with phenolic groups in the structure can be extensively metabolized in the liver (i.e., high first-pass metabolism) before they can enter the systemic circulation (FIG. 12). Thus, the locally bioavailable COX-2 inhibitors and their metabolites, mainly glucuronides and sulfates, are prevented from entering the systemic circulation, and therefore do not cause cardiovascular toxicity (FIG. 12).

From the foregoing description, one of ordinary skill in the art can easily ascertain the essential characteristics of this disclosure, and without departing from the spirit and scope thereof, can make various changes and modifications to adapt the disclosure to various usages and conditions. For example, references such as above, below, left, right, and the like are not meant to be limiting but rather as a guide for orientation of the referenced element to another element. A person of skill in the art should understand that certain of the above-described structures, functions, and operations of the above-described embodiments are not necessary to practice the present disclosure and are included in the description simply for completeness of an exemplary embodiment or embodiments. In addition, a person of skill in the art should understand that specific structures, functions, and operations set forth in the referenced patents and publications can be practiced in conjunction with the present disclosure, but they are not essential to its practice.

All of the compositions and methods disclosed and claimed herein can be made and executed without undue experimentation in light of the present disclosure. While the compositions and methods of this disclosure have been described in terms of preferred embodiments, it will be apparent to those skilled in the art that variations can be applied to the compositions and methods and in the steps or in the sequence of steps of the methods described herein without departing from the concept, spirit and scope of the disclosure. More specifically, it will be apparent that certain agents which are chemically related can be substituted for the agents described herein while the same or similar results would be achieved. All such similar substitutes and modifications apparent to those skilled in the art are deemed to be within the spirit, scope and concept of the disclosure as defined by the appended claims.

REFERENCES

1. Williams, C. S., M. Mann, and R. N. DuBois, The role of cyclooxygenases in inflammation, cancer, and development. Oncogene, 1999. 18(55): p. 7908-7916.

2. Gupta, R. A. and R. N. DuBois, Colorectal cancer prevention and treatment by inhibition of cyclooxygenase-2. Nat Rev Cancer, 2001. 1(1): p. 11-21.
3. Kawamori, T., C. V. Rao, K. Seibert, and B. S. Reddy, Chemopreventive Activity of Celecoxib, a Specific Cyclooxygenase-2 Inhibitor, against Colon Carcinogenesis. Cancer Research, 1998. 58(3): p. 409-412.
4. Solomon, S. D., J. J. V. McMurray, M. A. Pfeffer, J. Wittes, R. Fowler, P. Finn, W. F. Anderson, A. Zauber, E. Hawk, and M. Bertagnolli, Cardiovascular Risk Associated with Celecoxib in a Clinical Trial for Colorectal Adenoma Prevention. New England Journal of Medicine, 2005. 352(11): p. 1071-1080.
5. Solomon, S. D., J. Wittes, P. V. Finn, R. Fowler, J. Viner, M. M. Bertagnolli, N. Arber, B. Levin, C. L. Meinert, B. Martin, J. L. Pater, P. E. Goss, P. Lance, S. Obara, E. Y. Chew, J. Kim, G. Arndt, E. Hawk, and f.t.C.T.S.A. Group, Cardiovascular Risk of Celecoxib in 6 Randomized Placebo-Controlled Trials: The Cross Trial Safety Analysis. Circulation, 2008. 117(16): p. 2104-2113.
6. Davies, N., A. McLachlan, R. Day, and K. Williams, Clinical Pharmacokinetics and Pharmacodynamics of Celecoxib. Clinical Pharmacokinetics, 2000. 38(3): p. 225-242.
7. Stempak, D., J. Gammon, J. Klein, G. Koren, and S. Baruchel, Single-dose and steady-state pharmacokinetics of celecoxib in children[ast]. Clin Pharmacol Ther, 2002. 72(5): p. 490-497.
8. Berenson, A. Merck Agrees to Settle Vioxx Suits for $4.85 Billion. 2007; Available from: http://www.nytimes.com/2007/11/09/business/09merck.html?_r=0.
9. Sun, S. X., K. Y. Lee, C. T. Bertram, and J. L. Goldstein, Withdrawal of COX-2 selective inhibitors rofecoxib and valdecoxib: impact on NSAID and gastroprotective drug prescribing and utilization. Current Medical Research & Opinion, 2007. 23(8): p. 1859-1866.
10. Lee, W. M., Acetaminophen and the U.S. acute liver failure study group: Lowering the risks of hepatic failure. Hepatology, 2004. 40(1): p. 6-9.
11. Hu, M., Commentary: Bioavailability of Flavonoids and Polyphenols: Call to Arms. Molecular Pharmaceutics, 2007. 4(6): p. 803-806.
12. Chen, J., S. Wang, X. Jia, S. Bajimaya, H. Lin, V. H. Tam, and M. Hu, DISPOSITION OF FLAVONOIDS VIA RECYCLING: COMPARISON OF INTESTINAL VERSUS HEPATIC DISPOSITION. Drug Metabolism and Disposition, 2005. 33(12): p. 1777-1784.
13. Yang, Z., K. Kulkarni, W. Zhu, and M. Hu, Bioavailability and pharmacokinetics of genistein: mechanistic studies on its ADME. Anticancer Agents Med Chem, 2012. 12(10): p. 1264-80.
14. Kemp, D. C., P. W. Fan, and J. C. Stevens, Characterization of Raloxifene Glucuronidation in Vitro: Contribution of Intestinal Metabolism to Presystemic Clearance. Drug Metabolism and Disposition, 2002. 30(6): p. 694-700.
15. Paulson, S. K., M. B. Vaughn, S. M. Jessen, Y. Lawal, C. J. Gresk, B. Yan, T. J. Maziasz, C. S. Cook, and A. Karim, Pharmacokinetics of Celecoxib after Oral Administration in Dogs and Humans: Effect of Food and Site of Absorption. Journal of Pharmacology and Experimental Therapeutics, 2001. 297(2): p. 638-645.
16. Brenna, Ø., M. W. Furnes, I. Drozdov, A. van Beelen Granlund, A. Flatberg, A. K. Sandvik, R. T. M. Zwiggelaar, R. Marvik, I. S. Nordrum, M. Kidd, and B. I. Gustafsson, Relevance of TNBS-Colitis in Rats: A Methodological Study with Endoscopic, Histologic and Transcriptomic Characterization and Correlation to IBD. PLoS ONE, 2013. 8(1): p. e54543.
17. Kankuri, E., K. Vaali, R. Korpela, I. Paakkari, H. Vapaatalo, and E. Moilanen, Effects of a COX-2 preferential agent nimesulide on TNBS-induced acute inflammation in the gut. Inflammation, 2001. 25(5): p. 301-10.
18. Stella, V. J. and Q. He, Cyclodextrins. Toxicologic Pathology, 2008. 36(1): p. 30-42.
19. Folch-Cano, C., M. Yazdani-Pedram, and C. Olea-Azar, Inclusion and functionalization of polymers with cyclodextrins: current applications and future prospects. Molecules, 2014. 19(9): p. 14066-79.
20. Chen, J., H. Lin, and M. Hu, Metabolism of Flavonoids via Enteric Recycling: Role of Intestinal Disposition. Journal of Pharmacology and Experimental Therapeutics, 2003. 304(3): p. 1228-1235.
21. Tang, C., M. Shou, Q. Mei, T. H. Rushmore, and A. D. Rodrigues, Major Role of Human Liver Microsomal Cytochrome P450 2C9 (CYP2C9) in the Oxidative Metabolism of Celecoxib, a Novel Cyclooxygenase-II Inhibitor. Journal of Pharmacology and Experimental Therapeutics, 2000. 293(2): p. 453-459.
22. Grosser, T., S. Fries, and G. A. FitzGerald, Biological basis for the cardiovascular consequences of COX-2 inhibition: therapeutic challenges and opportunities. J Clin Invest, 2006. 116(1): p. 4-15.

The invention claimed is:

1. A tetra-cyclic Cox-II inhibitor having the structure:

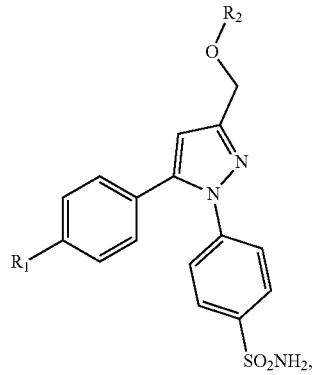

wherein $R_1$ is —$CH_3$, and wherein $R_2$ is a substituted benzylic ring, wherein the substituent is 2'—OH or 2'—$OCH_3$.

* * * * *

UNITED STATES PATENT AND TRADEMARK OFFICE
CERTIFICATE OF CORRECTION

PATENT NO. : 11,202,773 B2
APPLICATION NO. : 15/568195
DATED : December 21, 2021
INVENTOR(S) : Ming Hu Page 1 of 1

It is certified that error appears in the above-identified patent and that said Letters Patent is hereby corrected as shown below:

In the Specification

1. In Column 23, in Formula 5, Line 1, delete " 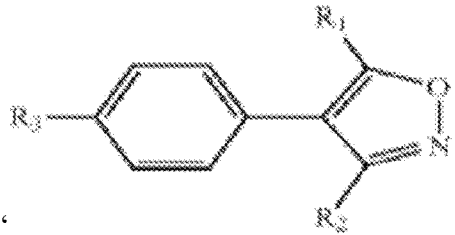 " and insert -- 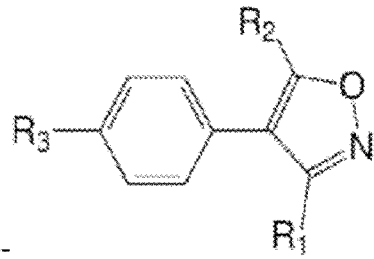 --, therefor.
2. In Column 25, Line 28, delete "$C(R_7)(R_8)(O_{1\text{-}4}alkyl)$" and insert -- $C(R_7)(R_8)(O\text{-}C_{1\text{-}4}alkyl)$ --, therefor.
3. In Column 29, Line 8, delete "0.1 μg/mL" and insert -- 0.1 μg/mL LPS --, therefor.

Signed and Sealed this
Fifth Day of April, 2022

Drew Hirshfeld
*Performing the Functions and Duties of the
Under Secretary of Commerce for Intellectual Property and
Director of the United States Patent and Trademark Office*